(12) United States Patent
Burrows et al.

(10) Patent No.: US 6,723,695 B1
(45) Date of Patent: Apr. 20, 2004

(54) CTL EPITOPES FROM EBV

(75) Inventors: Scott Renton Burrows, Bald Hills (AU); Rajiv Khanna, Herston (AU); Martina Alison Sherritt, Kedron (AU)

(73) Assignees: Council of the Queensland Institute of Medical Research, Queensland (AU); Commonwealth Scientific and Industrial Research Organisation of Limestone Avenue, Campbell Australian Capital Territory (AU); The University of Melbourne of Royal Parade, Victoria (AU); Walter and Elisa Hall Institute of Medical Research of Royal Melbourne Hospital, Victoria (AU); CSL Limited, Victoria (AU)

( * ) Notice: Subject to any disclaimer, the term of this patent is extended or adjusted under 35 U.S.C. 154(b) by 0 days.

(21) Appl. No.: 09/462,453

(22) PCT Filed: Jul. 10, 1998

(86) PCT No.: PCT/AU98/00531
§ 371 (c)(1),
(2), (4) Date: May 30, 2000

(87) PCT Pub. No.: WO99/02550
PCT Pub. Date: Jan. 21, 1999

(30) Foreign Application Priority Data

Jul. 10, 1997 (AU) .............................................. PO7841

(51) Int. Cl.[7] .......................... A61K 38/00; C07K 7/00; C07K 5/00; C07H 21/04; C12N 15/74
(52) U.S. Cl. .......................... 514/2; 530/300; 530/327; 530/328; 536/23.1; 435/320.1
(58) Field of Search .......................... 424/186.1, 202.1, 424/230.1, 281.1; 530/300; 536/23.72, 23.1; 514/2; 500/327, 328; 435/320.1

(56) References Cited

U.S. PATENT DOCUMENTS 5,869,453 A * 2/1999 Moss et al. .................... 514/16

FOREIGN PATENT DOCUMENTS

| AU | A-82073/87 | 6/1988 |
| EP | 0173254 | 3/1986 |
| WO | WO 93/19092 | 9/1993 |
| WO | WO 95/24925 | 9/1995 |
| WO | WO 95/284488 | * 10/1995 |
| WO | WO 96/03144 | 2/1996 |
| WO | WO 96/22999 | 8/1996 |
| WO | WO 97/45444 | 12/1997 |

OTHER PUBLICATIONS

Greenspan et al. Nature Biotechnology. 1999; 7:936–937.*
Lee et al. Journal of Virology. 1993; 67 (12): 7428–7435.*
Bharadwaj et al. (Vaccine. 2001; 19: 3769–3777.*
Sequence alignment of SEQ ID NO: 26 with WO 95/28488, Spaete et al. Geneseq database, first entered Jan. 18, 1996. Accessio No: AAR80144.*
Sequence alignment of SEQ ID NO: 27 with WO 95/28488, Spaete et al. Geneseq database, first entered Jan. 18, 1996. Accessio No: AAR80144.*
Khanna et al. Journal of Experimental Medicine. 1992; 176 (1): 169–76.*
Moss et al. CIBA Foundation Symposium. 1994; 187; 4–13; discussion 13–20. Ref: 13. Abstract only.*
Kerr et al. Journal of Virology. 1996; 70 (12) 8858–64.*
Rickinson et al. Annual Review of Immunology. 1997; 15: 405–31.*
Thomson et al. Journal of Immunology. 1998; 160 (4): 1717–23.*
Khanna et al. Journal of Immunology. 1999; 162 (5): 3063–9.*
Jackman et al. Vaccine. 1999; 17 (7–8): 660–8.*
Bharadwaj et al. Vaccine. 2001; 19 (27): 3769–77.*
Khanna et al., "Identification of cytotoxic t cell epitopes within Epstein–barr virus (EBV) oncogene latent membrane protein 1 (LMP1): evidence for HLA A2 supertype–restricted immune recognition of EBV–infected cells by LMP1–specific cytotoxic T lymphocytes," *Eur. J. Immunol.*, 28:451–458, 1998.
Wallace et al., "Identification of Two T–Cell Epitopes on the candidate epstein–barr virus vaccine glycoprotein gp340 recognized by CD4+ t–cells clones," *J Virol*, 65:3821–3828, 1991.
Lee et al., "Conserved CTL Epitopes Within EBV Latent Membrane Protein 2," J Immun., 158:3325–3334, 1997.
Appolloni et al., "Sequence variation of cytotoxic T cell epitopes in different isolates of Epstein–Barr virus," *Eur. J. Imunol.*, 22:183–189, 1992.
Burrows et al., "An Epstein–Barr virus–specific cytotoxic T cell epitope in EBV nuclear antigen 3 (EBNA 3)," *J. Exp. Med.*, 171:345–349, 1990.

(List continued on next page.)

Primary Examiner—James Housel
Assistant Examiner—Shanon Foley
(74) Attorney, Agent, or Firm—Fulbright & Jaworski

(57) ABSTRACT

The present invention provides cytotoxic Epstein-Barr virus (EBV) T-cell epitopes derived from EBV structural antigens. Preferred epitopes include YLLEMLWRL (SEQ ID NO:1), YFLEILWGL (SEQ ID NO:32), YLLEILWRL (SEQ ID NO:33), YLQQNWWTL (SEQ ID NO:6), LLLALLFWL (SEQ ID NO:2), LLVDLLWLL (SEQ ID NO:3), LLLIAL-WNL (SEQ ID NO:4), WLLLFLAIL (SEQ ID NO:5), TLLVDLLWL (SEQ ID NO:7), LLWLLLFLA (SEQ ID NO:8), ILLIIALYL (SEQ ID NO:9), VLFIFGCLL (SEQ ID NO:10), RLGATIWQL (SEQ ID NO:11), ILYFIAFAL (SEQ ID NO:15), SLVIVTTFV (SEQ ID NO:17), LMII-PLINV (SEQ ID NO:20), TLFIGSHVV (SEQ ID NO:24), LIPETVPYI (SEQ ID NO:26), VLQWASLAV (SEQ ID NO:27) and QLTPHTKAV (SEQ ID NO:29). The present invention also provides methods of treating or preventing EBV infection in subjects which involve administration of EBV cytotoxic T-cell epitopes.

17 Claims, 25 Drawing Sheets

OTHER PUBLICATIONS

Burrows et al., "An Epstein–Barr virus–specific cytotoxic T–cell epitope present on A– and B–type transformants," *Journal of Virology*, 64:3974–3976, 1990.

Burrows et al., "Unusually high frequency of Epstein–Barr virus genetic variants in Papua, New Guinea that can escape cytotoxic T–cell recognition: implications for virus evolution," *Journal of Virology*, 70:2490–2496, 1996.

Fields et al., (editors in chief), "Fundamental Virology," *Lippincott–Raven Publishers*, Third edition, p. 1121, 1996.

Franken et al., "Comparative analysis identifies conserved tumor necrosis factor receptor–associated factor 3 binding sites in the human and simian Epstein–Barr virus oncogene LMP1," 70:7819–7826, 1996.

Hu et al., "Isolation and sequencing of the Epstein–Barr virus BNLF–1 gene (LMP1) from a Chinese nasopharyngeal carcinoma," *Journal of General Virology*, 72:2399–2409, 1991.

Kerr et al., "Identification of type b–specific and cross–reactive cytotoxic t–lymphocyte response to Epstein–Barr virus," *Journal of Virology*, 70:8858–8864, 1996.

Lees et al., "The Epstein–Barr virus candidate vaccine antigen gp340/220 is highly conserved between virus types A and B[1]," *Virology*, 195:578–586, 1993.

Mackett et al., "Immunisation of common marmosets with vaccinia virus expressing Epstein–Barr virus (EBV) gp340 and challenge with EBV," *Journal of Medical Virology*, 50:263–271, 1996.

Murray et al., "Cross–recognition of a mouse H–2–peptide complex by human HLA–restricted cytotoxic T cells," *Eur. J. Immunol*, 20:659–664, 1990.

Oba et al., "Induction of antibodies to the Epstein–Barr virus glycoprotein gp85 with a synthetic peptide corresponding to a sequence in the BXLF2 open reading frame," *Journal of Virology*, 62:1108–1114, 1988.

Pothen et al., "Identification of T– and B–cell epitopes associated with a restricted component of the Epstein–Barr virus–induced early antigen complex," *Int. J. Cancer*, 53:199–204, 1993.

Suhrbier et al., "Modification of the carboxyl terminal group affects replacement set analysis of a cytotoxic T cell epitope," *Peptide Research*, 8:258–262, 1995.

Thorley–Lawson and Israelsohn, "Generation of specific cytotoxic T cells with a fragment of the Epstein–Barr virus–encoded p63/latent membrane protein," *Proc. Natl. Acad. Sci.*, 84:5384–5388, 1987.

* cited by examiner

Figure 6B

Figure 12

CTL EPITOPES FROM EBV

FIELD OF THE INVENTION

The present invention relates to methods of treating or preventing EBV infections. The present invention also relates to cytotoxic T-cell (CTL) epitopes within Epstein-Barr virus (EBV) structural and latent antigens, and to subunit vaccines and nucleic acid vaccines which include these epitopes.

BACKGROUND OF THE INVENTION

It is now well established that long-term protection from persistent viral infection requires the development of virus-specific memory T cells which recognize viral antigens in association with either class I or class II MHC molecules. Since immunization with whole viral proteins is unable to elicit an efficient CTL response, interest has been directed towards designing vaccines based on defined epitope sequences. This is particularly the case with oncogenic viruses, since individual viral genes introduced in recombinant vectors have the potential to initiate tumorgenic processes. Two broad approaches are currently being considered to design an effective vaccine for controlling Epstein-Barr virus (EBV) associated diseases (for review see ref. (7)). These include directing immune responses to either EBV structural antigens or latent antigens.

In the last few years, most of the vaccine development efforts have concentrated on the use of a subunit preparation of gp350 (recombinant and affinity purified) and have been directed towards blocking virus attachment to the target cell in the oropharyrix (31). The general approach has been to immunize cotton-top marmosets with gp350 and determine their ability to restrict the outgrowth of EBV-positive lymphomas in these animals. Indeed, highly purified gp350, when administered subcutaneously in conjunction with adjuvants (muramyl dipeptide or ISCONIS). induced high levels of serum neutralizing antibodies and inhibited tumor formation in cotton-top tamarins (32). A number of recombinant vectors including, vaccinia-gp350 and adenovirus 5-gp350 have also been successfully used in these animals to block tumor outgrowth (33). The precise mechanism by which gp350 affords protection from lymphomas in cotton-top tamarins remains unclear. The fact that development of neutralizing antibody titres in vaccinated animals does not always correlate with protection indicates that gp350-specific T cell-mediated immune responses may also have an effector role (34). Furthermore, Yao and colleagues (35) showed that very low levels of neutralizing anti-gp350 antibodies are present in the saliva of healthy EBV-immune donors, which suggests that such antibodies are unlikely to be the basis of long-term immunity in healthy seropositive individuals. It has been postulated that gp350 specific T cell-mediated immune responses may have an effector role in protection. There has been no identification to date, however, of CTL epitopes within the EBV structural antigens.

Post-transplant lymphoproliferative disease (PTLD) that arises in organ transplant patients is an increasingly important clinical problem. Histological analysis of PTLD shows a quite complex clonal diversity ranging from polymorphic B lymphocyte hyperplasia to malignant monoclonal lymphoma. This range of pathology encompasses the collective term PTLD while the lymphomas are frequently referred to as immunoblastic lymphomas(IL). This condition is clearly associated with the proliferation of Epstein-Barr virus (EBV) infected B cells which are carried for life in all previously infected individuals (about 80% of adults and 20% of children 7 years) (45, 46, 47, 49). These EBV-infected B cells are normally restricted in their growth in vitro and in vivo by virus-specific cytotoxic T cells (CTLs) which recognise epitopes included within the EBV latent proteins (see below) (48). Immunosuppression inhibits these specific CTL and results in an expansion of the pool of EBV-infected B cells and the emergence of the clinical problems associated with PTLD. It is known that the individuals at greatest risk of PTLD are EBV seronegative recipients who receive a transplant from a seropositive donor (Crawford and Thomas, 1993). Immunisation of EBV seronegative graft recipients prior to engraftment will greatly reduce the risk of PTLD.

The role of the immune system in the rejection of virus-associated cancers has also been the subject of intense study recently. The hypothesis under investigation is that many neoplasms express viral antigens that should potentially enable them to be recognized and destroyed by the immune system, including both T helper cells and cytotoxic T lymphocytes (CTL). There is now compelling evidence that most of the Epstein-Barr virus (EBV)-associated malignancies escape this potent virus-specific CTL response by restricting viral gene expression (7.20,21). For malignancies such as nasopharyngeal carcinoma (NTC) and Hodgkin's disease (HD). EBV nuclear antigen 1 (EBNA1) and latent membrane protein 1 (LMP1) are the only antigens consistently expressed and are therefore the potential target antigens for any future vaccine designed to control these tumors (3,28). Since it is well established that immunization with whole viral proteins does not elicit an efficient CTL response, interest has been directed towards developing peptide vaccines based on defined epitope sequences.

SUMMARY OF THE INVENTION

Results obtained by the present inventors indicate that CTL epitopes within EBV structural and latent proteins may be effective in providing antiviral immunity against EBV infection. In particular, the present inventors have analysed the latent antigen LMP1 sequence, using peptide stablization assays, and found that this antigen includes potential CTL epitopes. Following in vitro activation with these peptides, both polyclonal and clonal CTLs from HLA A2-positive donors showed strong reactivity against target cells expressing the LMP1 antigen. Moreover. lvmphoblastoid cell lines (LCL). expressing different HLA A2 supertypes were efficiently recognized by these CTLs, a result that has important implications for the design of an anti-viral vaccine aimed at protecting different ethnic populations.

The present inventors have also found that CTLs from acute infectious mononucleosis (IM) patients display strong reactivity against the EBV structural antigens gp85 and gp350. In addition, specific CTL epitopes within EBV structural antigens gp85 and gp350 have been identified for the first time. Importantly, prior immunisation of HLA A2/$K^b$ transgenic mice with these gp350 and gp85 CTL epitopes induced a strong epitope-specific CTL response and afforded protection against gp85- or gp350-expressing vaccinia virus challenge. These results provide evidence, for the first time, of the existence of CTL epitopes in EBV structural proteins and show that they may be used for establishing strong anti-viral immunity against EBV infection.

Accordingly, in a first aspect the present invention provides a cytotoxic Epstein-Barr virus (EBV) T-cell epitope, the epitope being derived from an EBV structural antigen.

In a preferred embodiment of the first aspect of the present invention, the EBV structural antigen is gp85 or gp350.

In a second aspect the present invention provides a cytotoxic Epstein-Barr virus T-cell epitope, the epitope being selected from the group consisting of YLLEMLWRL (SEQ ID NO:1), YFLEILWGL (SEQ ID NO:32), YLLEIL-WRL (SEQ ID NO:33), YLQQNWWTL (SEQ ID NO:6), LLLALLFWL (SEQ ID NO:2), LLVDLLWLL (SEQ ID NO:3), LLLIALWNL (SEQ ID NO:4), WLLLFLAIL (SEQ ID NO:5), TLLVDLLWL (SEQ ID NO:7), LLWLLLFLA (SEQ ID NO:8), ILLIIALYL (SEQ ID NO:9), VLFIFGCLL (SEQ ID NO:10), RLGATIWQL (SEQ ID NO:11), ILYFIA-FAL (SEQ ID NO:15), SLVIVTTFV (SEQ ID NO:17), LMIIPLINV (SEQ ID NO:20), TLFIGSHVV (SEQ ID NO:24), LIPETVPYI (SEQ ID NO:26), VLQWASLAV (SEQ ID NO:27) and QLTPHTKAV (SEQ ID NO:29).

In a third aspect the present invention provides a subunit vaccine including a cytotoxic Epstein-Barr virus (EBV) T-cell epitope according to the first aspect of the present invention.

In a preferred embodiment, the subunit vaccine includes at least one T-cell epitope selected from the group consisting of YLLEMILWRL (SEQ ID NO:1), YFLEILWGL (SEQ ID NO:32), YLLEILWRL (SEQ ID NO:33), YLQQNWWTL (SEQ ID NO:6). LLLALLFWL (SEQ ID NO:2). LLVDLL-WLL (SEQ ID NO:3), LLLIALWNL (SEQ ID NO:4), WLLLFLAIL (SEQ ID NO:5), TLLVDLLWL (SEQ ID NO:7). LLWLLLFLA (SEQ ID NO:8), ILLIIALYL (SEQ ID NO:9), VLFIFGCLL (SEQ ID NO:10), RLGATIWQL (SEQ ID NO:11), ILYFIAFAL (SEQ ID NO:15). SLVIVT-TFV (SEQ ID NO:17), LMIIPLINV (SEQ ID NO:20), TLFIGSHVV (SEQ ID NO:24). LIPETVPYI (SEQ ID NO:26). VLQWASLAV (SEQ ID NO:27) and QLTPHT-KAV (SEQ ID NO:29).

In a preferred aspect of the present invention the epitope is selected from the group consisting of YLLEMLWRL (SEQ ID NO:1). YLQQNWWTL (SEQ ID NO:6). YFLEIL-WGL (SEQ ID NO:32), YLLEILWRL (SEQ ID NO:33). SLVIVTTFV (SEQ ID NO:17), LMIIPLINV (SEQ ID NO:20). TLFIGSHVV (SEQ ID NO:24), and VLQ-WASLAV (SEQ ID NO:27).

In a further preferred embodiment, the subunit vaccine includes one or more additional cytotoxic EBV T-cell epitopes. The additional cytotoxic EBV T-cell epitope(s) may be selected from those described in WO 97/45444, the entire contents of which are incorporated herein by reference.

In a further preferred form of the present invention the vaccine includes a water-in-oil formulation. It is further preferred that the vaccine includes at least one antigen to which the individual will mount an anamniestic response in addition to the at least one cytotoxic T-cell epitope.

The at least one antigen is preferably selected from the group consisting of tetanus toxoid, diphtheria toxoid, Bordetella pertussis antigens, poliovirus antigens, purified protein derivative (PPD), gp350 protein (Thorley-Lawson, D. A. and Poodry, C. A. (1982). Identification and isolation of the main component (gp35G-gp220) of Epstein-Barr virus responsible for generating neutralizing antibodies in vivo. *J. Virol.* 43, 730–736), helper epitopes and combinations thereof and is preferably tetanus toxoid.

It is preferred that the water-in-oil formulation is Montanide ISA 720. Additional information regarding this formulation can be found in WO 95/24926, the disclosure of which is incorporated herein by cross reference.

The subunit vaccine may also be formulated using ISCOMs. Further information regarding ISCOMs can be found in Australian Patent Nos. 558258, 590904, 632067, 589915, the disclosures of which are included herein by cross reference.

In a fourth aspect the present invention provides an isolated nucleic acid sequence encoding a cytotoxic Epstein-Barr virus (EBV) T-cell epitope according to the first aspect of the present invention.

In a preferred embodiment, the isolated nucleic acid sequence encodes at least one of the cytotoxic T-cell epitopes selected from the group consisting of YLLEML-WRL (SEQ ID NO:1), YFLEILWGL (SEQ ID NO:32), YLLEILWRL (SEQ ID NO:33). YLQQNWWTL (SEQ ID NO:6), LLLALLFWL (SEQ ID NO:2). LLVDLLWLL (SEQ ID NO:3), LLLIALWNL (SEQ ID. NO:4), WLLL-FLAIL (SEQ ID NO:5), TLLVDLLWL (SEQ ID NO:7). LLWLLLFLA (SEQ ID NO:8), ILLIIALYL (SEQ ID NO:9), VLFIFGCLL (SEQ ID NO:10), RLGATIWQL (SEQ ID NO:11), ILYFIAFAL (SEQ ID NO:15), SLVIVTTFV (SEQ ID NO:17). LMIIPLINV (SEQ ID NO:20), TLFIG-SHVV (SEQ ID NO:24), LIPETVPYI (SEQ ID NO:26), VLQWASLAV (SEQ ID NO:27) and QLTPHTKAV (SEQ ID NO:29).

As will be appreciated by those skilled in the field the nucleic acid sequence can be delivered as naked nucleic acid or using a suitable viral or bacterial vectors. Suitable bacterial vectors include the bacteria Salmonella spp. Suitable viral vectors include, for example, retroviral vectors, adenoviral vectors and vaccinia vectors. An example of a suitable vaccinia vector is a modified Vaccinia Ankara vector.

Vectors suitable for delivery of nucleic acid sequences have previously been described. For example, alphavirus vectors have become widely used in basic research to study the structure and function of proteins and for protein production purposes. Development of a variety of vectors has made it possible to deliver foreignsequences as naked RNA or DNA, or as suicide virus particles produced using helper vector strategies. Preliminary reports also suggest that these vectors may be useful for in vivo applications where transient, high-level protein expression is desired, such as recombinant vaccines. The initial studies have already shown that alphavirus vaccines can induce strong humoral and cellular immune responses with good immunological memory and protective effects. See, for example, Tubulekas I., Berglund P., Fleeton M., and Liljestrom P. (1997) Alphavirus expression vectors and their use as recombinant vaccines:a minireview, *Genie* 190(1):191–195.

Recombinant pox viruses have been generated for vaccination against heterologous pathogens. Amongst these, the following are notable examples. (i) The engineering of the Copenhagen strain of vaccinia virus to express the rabies virus glycoprotein. When applied in baits, this recombinant has been shown to vaccinate the red fox in Europe and raccoons in the United States, stemming the spread of rabies virus infection in the wild. (ii) A fowlpox-based recombinant expressing the Newcastle disease virus fusion and hemagglutinin glycoproteins has been shown to protect commercial broiler chickens for their lifetime when the vaccine was administered at 1 day of age, even in the presence of maternal immunity against either the Newcastle disease virus or the pox vector. (iii) Recombinants of canarypox virus, which is restricted for replication to avian species, have provided protection against rabies virus challenge in cats and dogs against canine distemper virus, feline leukemia virus, and equine influenza virus disease. In humans, canarypox virus-based recombinants expressing antigens from rabies virus. Japanese encephalitis virus, and HV have been shown to be safe and immunogenic. (iv) A highly attenuated vaccinia derivative, NYVAC has been engineered to express antigens from both animal and human pathogens. Safety and immunogeniicity of NYVAC-based recombinants expressing the rabies virus glycoprotein, a polyprotein from Japanese encephalitis virus, and seven antigens from Plasmodium falciparum have been demonstrated to be safe and immunogenic in early human vaccine studies. See, for example, Paoletti E. (1996) Applications of pox virus vectors to vaccination:an update, *Proc Natl Acad Sci U S A*, 93(21):11349–11353.

Progress towards effective vaccines to control internal parasites, especially those affecting mucosal compartments, has been inhibited by the combined problems of the antigenic complexity of parasites and the lack of understanding of the host response. However, the accumulation of information regarding regulation of mucosal immunity has enabled a reappraisal of vaccination options to provide appropriate mucosal effector responses. The pivotal role of T cell influences, and in particular the contribution of cytokine signals, has been clearly established from in vitro studies, but data emerging from our laboratories provide evidence for these effects in vivo. We have demonstrated the role of T cells in determining the outcome of an intestinal response and propose a role for local Th2 cytokine production in this regard. To support this proposition, the distribution of cytokine mRNA has been determined by in situ hybridisation techniques in normal and parasitised animals. Further, we have shown that in the absence of Th2 cytokines (using gene knockout animals) mucosal responses are grossly deficient:we have also shown that this defect can be overcome by vector-directed gene therapy. These studies have indicated that new-mucosal immunisation opportunities exist by combining traditional immunisation approaches with strategies to upregulate local cytokine production. -However, the success of these new strategies will depend on selection of highly immunogenic subunit antigens, coupled with techniques for cytokine manipulation and delivery with appropriate adjuvant/vehicle formulations. This paper reviews delivery technologies available to chaperone labile antigenic and genetic material to appropriate sites for mucosal stimulation after systemic or oral administration. See, for example, Sutter G. et al (1994) A recombinant vector derived from the host range-restricted and highly attenuated MVA strain of vaccinia virus stimulates protective immunity in mice to influenza virus. *Vaccine* 12:1032–1040; and Husband A. J Bao S., McClure S. J., Emery D. L., Ramsay A. J. ( 1996) Antigen delivery strategies for mucosal vaccines. Int J Parasitol 8–9:825–834.

Attenuated *Salmonella typhi* vaccine strain CVD 908, which harbors deletion mutations in aroC and aroD, has been shown to be well-tolerated and highly immunogenic, eliciting impressive serum antibody, mucosal IgA and cell-mediated immune responses. A further derivative prepared by introducing a deletion in htrA (which encodes a heat-shock protein that also has activity as a serine protease in CVD 908 resulted in CVD 908-htrA. In phase 1 clinical trials, CVD 908-htrA appears very attractive as a live oral vaccine candidate. Both CVD 908 and CVD 908-htrA are useful as live vector vaccines to deliver foreign antigens to the immune system. Conditions that enhance the expression and immunogenicity of foreign antigens carried by CVD 908 and CVD 908-htrA are being investigated. For a review of Salmonella vectors, see Levine M. M., Galen J., Barry E., Noriega F., Chatfield S., Sztein M., Dougan G. And Tacket C (1996) Attenuated Salmonella as live oral vaccines against typhoid fever and as live vectors, J Biotechnol 44(1–3) :193–196.

The isolated nucleic acid sequences may be in the form of nucleic acid vaccines. Further information regarding nucleic acid vaccines can be found in WO 96/03144 and in Suhrbier A (1997), Multi-epitope DNA vaccines, *Immunol Cell Biol* 75(4):402–408 the disclosures of which are incorporated herein by cross reference.

In a fifth aspect the present invention provides an isolated polypeptide, the polypeptide including at least one epitope according to the first or second aspects of the present invention.

The vaccines of the present invention may be used prophylactically or therapeutically.

The CTL epitopes of the present invention may be synthesised using techniques well known to those skilled in this field. For example, the CTL epitopes may be synthesised using solution synthesis or solid phase synthesis as described, for example, in Chapter 9 entitled "Peptide Synthesis" by Atherton and Sheppard which is included in a publication entitled "Synthetic Vaccines" edited by Nicholson and published by Blackwell Scientific Publications. Preferably a solid phase support is utilised which may be polystyrene gel beads wherein the polystyrene may be cross-linked with a small proportion of divinylbenzene (e.g. 1%) which is further swollen by lipophilic solvents such as dichloromethane or more polar solvents such as dimethylformamide (DNIF). The polystyrene may be functionalised with chloromethyl or anionomethyl groups. Alternatively, cross-linked and functionalised polydiniethyl-acrylamide gel is used which may be highly solvated and swollen by DNIF and other dipolar aprolic solvents. Other supports can be utilised based on polyethylene glycol which is usually grafted or otherwise attached to the surface of inert polystyrene beads. In a preferred form, use may be made of commercial solid supports or resins which are selected from PAL-PEG, PAK-PEG, KA, KR or TGR.

In solid state synthesis, use is made of reversible blocking groups which have the dual function of masking unwanted reactivity in the a-amino, carboxy or side chain functional groups and of destroying the dipolar character of amino acids and peptides which render them inactive. Such functional groups can be selected from t-butyl esters of the structure RCO—OCMe$_3$—CO—NHR which are known as t-butoxy carbonyl or ROC derivatives. Use may also be made of the corresponding benzyl esters having the structure RCO—OCH$_2$—C$_6$H$_s$ and urethanes having the structure C$_6$H$_5$CH$_2$O CO—NHR which are known as the benzyloxycarbonyl or Z-derivatives. Use may also be made of derivatives of fluorenyl methanol and especially the fluoreniylmethoxy carbonyl or Fmoc group. Each of these types of protecting group is capable of independent cleavage in the presence of one other so that frequent use is made, for example, of BOC-benzyl and Fmoc-tertiary butyl protection strategies.

Reference also should be made to a condensing agent to link the amino and carboxy groups of protected amino acids or peptides. This may be done by activating the carboxy group so that it reacts spontaneously with a free primary or secondary amine. Activated esters such as those derived from p-nitrophenol and pentafluorophenyl may be used for this purpose. Their reactivity may be increased by addition of catalysts such as 1-hydroxybenzotriazole. Esters of triazine DHBT (as discussed on page 215–216 of the above-mentioned Nicholson reference) also may be used. Other acylating species are formed in situ by treatment of the carboxylic acid (i.e. the Nα-protected amino acid or peptide) with a condensing reagent and are reacted immediately with the amino component (the carboxy or C-protected amino acid or peptide). Dicyclohexylcarbodiimide, the BOP reagent (referred to on page 216 of the Nicholson reference), O'Benzotriazole-N, N, N'N'-tetra methyl-uronium hexaflurophosphate (HBTU) and its analogous tetrafluroborate are frequently used condensing agents.

The attachment of the first amino acid to the solid phase support may be carried out using BOC-anino acids in any suitable manner. In one method BOC amino acids are attached to chloromethyl resin by warming the triethyl ammonium salts with the resin. Fmoc-amino acids may be coupled to the p-alkoxybenzyl alcohol resin in similar manner. Alternatively, use may be made of various linkage agents or "handles" to join the first amino acid to the resin. In this regard, p-hydroxymethyl phenylactic acid linked to aminomethyl polystyrene may be used for this purpose.

As will be readily appreciated by those skilled in the art the LMP1, gp85 and gp350 epitopes and vaccines of the present invention can be used to treat and to protect against EBV. Further, given the possible greater involvement of EBV infection in immnunocompromised individuals, the present invention may have particular application in the treatment and protection of individuals having decreased immune function, eg transplant patients. Importantly, the present inventors have found that EBV transformed lymphoblastoid cell lines expressing different HLA A2 supertypes are efficiently recognised by LMP1-specific CTL clones. This highlights the potential for the design of an antiviral vaccine aimed at treating and protecting different ethnic populations.

Accordingly, in a sixth aspect the present invention provides a method of preparing a composition for use in inducing CTLs in a subject, the method including admixing at least one epitope according to the first or second aspects of the present invention with at least one pharmaceutical acceptable carrier, diluent or excipient.

In a seventh aspect the present invention provides a method of reducing the risk of EBV infection in a subject which method includes administering to the subject an effective amount of:
(1) at least one CTL epitope according to the first or second aspects of the present invention;
(2) a subunit vaccine according to the third aspect of the present invention;
(3) a nucleic acid sequence according to the fourth aspect of the present invention:.
(4) a vector according to the fourth aspect of the present invention;
or
(5) a polypeptide according to the fifth aspect of the present invention.

In an eighth aspect the present invention provides a method of treating or preventing nasopharyngeal carcinoma or Hodgkin's disease in a subject which method includes administering to the subject an effective amount of at least one CTL epitope derived from an EBV structural or latent antigen.

By "effective amount" we mean a quantity of the epitope which is sufficient to induce or amplify a CTL response against an EBV antigen.

In a preferred embodiment of the eighth aspect of the present invention, the EBV structural antigen is gp83 or gp350 and the latent antigen is LMP1 or LMP2. In a further preferred embodiment the CTL epitope is an epitope as defined in the second aspect of the present invention.

The present inventors have also made the surprising finding that NPC cells which are recognised by CTL clones are subject to CTL lysis. This finding has important implications for the design of vaccines to control NPC tumours in vivo.

In an ninth aspect the present invention provides a method of treating or preventing growth of NPC or HD cells in a subject in need thereof which method includes administering to the subject at least one CTL epitope derived from an EBV structural or latent antigen.

In a preferred embodiment of the ninth aspect of the present invention, the EBV CTL epitopes are derived from the gp85 or gp350 -antigens. In a further preferred embodiment, the EBV CTL epitopes are derived from the LMP1 or LMP2 antigens. Preferably, the CTL epitopes are derived from the LMP1 antigen.

In a tenth aspect the present invention provides a method of treating or preventing the growth of NPC or HD) cells in a first subject which method includes transferring to the subject EBV-specific CTLs which recognise NPC or HD cells.

In a preferred embodiment the EBV-specific CTLs are obtained from NPC patients by in vitro stimulation of CTLs by exposure to EBV CTL epitopes. Alternatively, the EBV-specific CTLs may be obtained from a second subject, wherein the second subject is infected with EBV but does not have NPC.

In a further preferred embodiment of the tenth aspect of the present invention, the EBV-specific CTLs are LMP1 and/or LMP2-specific CTLs.

In an eleventh aspect the present invention provides a method of reducing the risk of infectious mononucleosis or post transplantation lymphoproliferative disease in a subject which method includes administering to the subject an effective amount of:
(1) at least one CTL epitope according to the first or second aspects of the present invention;
(2) a subunit vaccine according to the third aspect of the present invention;
(3) a nucleic acid sequence according to the fourth aspect of the present invention;
(4) a vector according to the fourth aspect of the present invention;
or
(5) a polypeptide according to the fifth aspect of the present invention.

The terms "comprise", "comprises" and "comprising" as used throughout the specification are intended to refer to the inclusion of a stated component or feature or group of components or features with or without the inclusion of a further component or feature or group of components or features.

In order that the nature of the present invention may be more clearly understood forms thereof will now be described with reference to the following examples and figures.

BRIEF DESCRIPTION OF THE FIGURES

FIG. 12:Prior immunisation of HLA A2/Kb mice with gp85 or gp350 CTL epitopes affords protection against recombinant vaccinia virus challenge. Groups of female A2/Kb transgenic mice, either unimmunized or immunized with CTL epitopes, were challenged with Vacc.gp85 and Vacc.gp350 intraperitonealy. After four days of challenge, these animals were sacrificed and vaccinia titre measured in both ovaries by plaque assay on confluent CV1 cells. X-axis shows peptides used for immunization, while Y-axis shows Niean +/− SE vaccinia virus titre in naive and peptide immunized mice. Recombinant vaccinia virus used for challenge in these animals is shown in each panel of the figure.

DETAILED DESCRIPTION OF THE INVENTION

EXAMPLE 1

Figure 1:
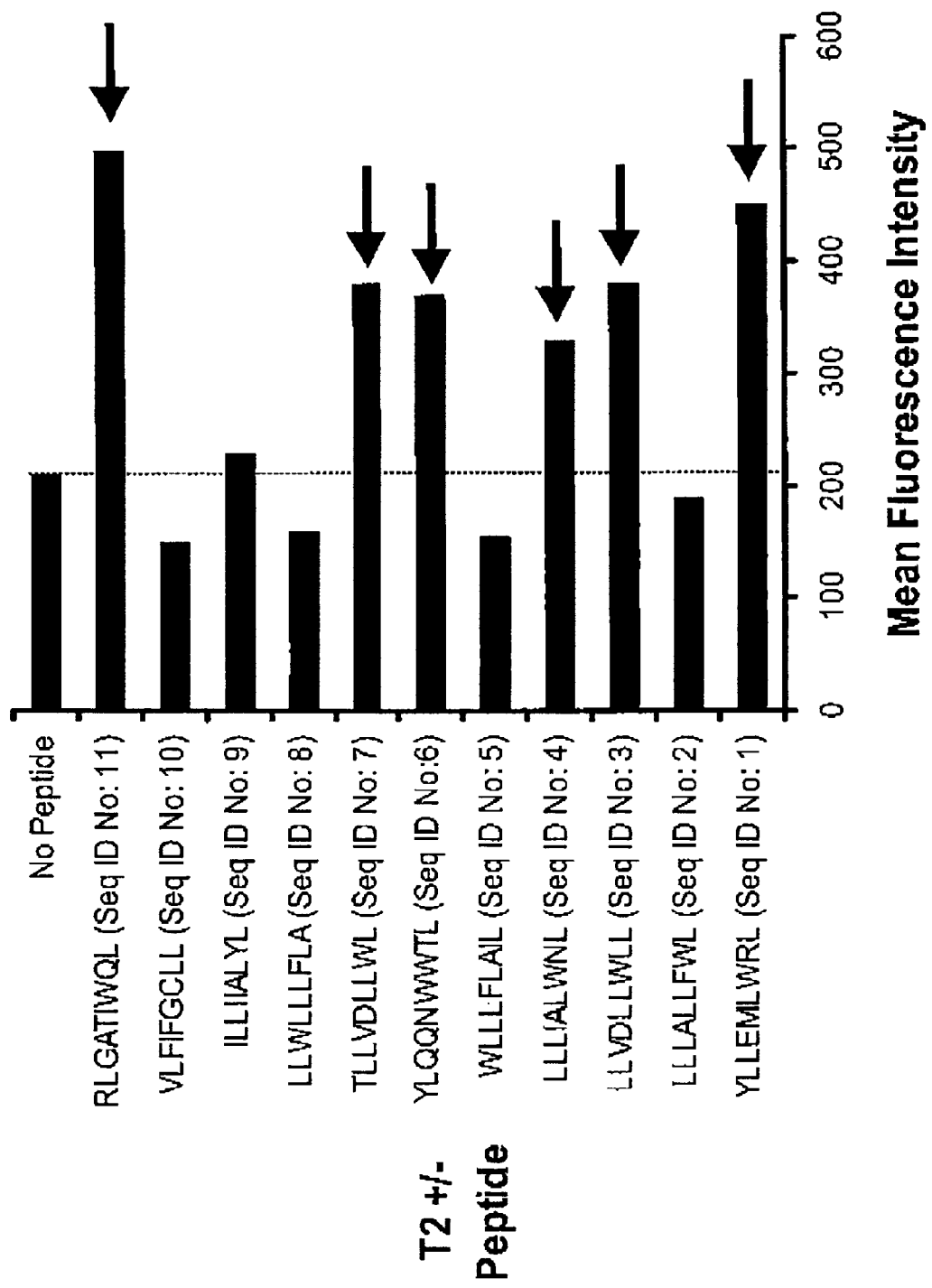
FIG. 1:MHC stablization analysis on T2 cells using potential HLA A2 binding peptides within LMP1. T2 cells were initially incubated with 200 µl of each of the peptides (200 µg/ml) for 14–16h at 26° C. followed by incubation at 37° C. for 2–3h. HLA A2 expression on these cells was analysed by FACS using the BB7.2 antibody. The dotted line indicates the background mean fluorescence intensity for HlAA2 on T2 cells without any peptide. The LMP1 peptides showing significant stablization of HLA A2 molecules on T2 cells are indicated by arrows.

Niaterials and Niethods
Establishment and Maintenance of Cell Lines

LCLs were established from sero-positive donors by exogenous virus transformation of peripheral B cells using the B95.8 (Type 1) or Ag876 (Type 2) virus isolates. In addition, LCLs transformed with the B95.8 isolate and expressing different HLA A2 supertypes were also used in this study (12th Histocompatability workshop cell panel; EACC). The peptide transporter (TAP)-negative B×T hybrid cell line 174×CEM.T2 (referred to as T2) (22) were used for peptide stablization assays. All cell lines were routinely maintained in RPMI 1640 containing 2 mM glutamine, 100 IU/ml penicillin and 100 $\mu$g/ml streptomycin plus 10% foetal calf serum (FCS) (growth medium). Long-term cultures of EBV-negative normal B cell blasts were established as previously described using the CD40 system (referred to as CD40 B cells) (12).

The Burkitt's lymphoma (BL) cell lines, BJAB.gpti, BJAB.MTLM6, MUTU cl.59 and N=MUTU cl.216 were used in this study. These were derived from patients with non-endemic or endemic BL. BJAB.MTLM6 and N=MUTU cl.59 have previously been shown to express LMP1, while BJAB.gpt1 and MUTU cl.216 are negative for LMP1 (5,27). These BL cell lines were routinely maintained in growth medium.

To generate phytohaemagglutinin (PHA) blasts, peripheral blood mononuclear (PBMC) cells were stimulated with PHA (Commonwealth Serum Laboratories, Melbourne) and after 3 days, growth medium containing MLA 144 supernatant and rIL-2 was added (2). PHA blasts were propagated with bi-weekly replacement of IL-2 and NILA supernatant (no further PHA added) for up to 6 weeks.

Virus Isolates

To isolate resident EBV, spontaneous LCLs were established from a panel of 12 unrelated healthy EBV-seropositive donors by spontaneous outgrowth from PBMC cultured in the presence of 0.1 $\mu$g/ml cyclosporin A (19). In addition, virus isolates from eight different NPC samples (from Southeast Asia) were directly sequenced from biopsy material. These isolates were classified as type 1 EBV based on the DNA sequence divergence within the BAM H1 WYH and E regions of the genome (23,24).

PCR and DNA Sequencing of CTL Epitopes

Specific oligonucleotide primers flanking the DNA region encoding the LMP1 epitope were selected for PCR amplification. The resulting PCR products were purified using QIAquick spin columns (Qiagen Inc. Chatsworth, Calif.) and sequenced in both directions using a PRISM ready reaction dyedeoxy terminator cycle sequencing kit (Applied Biosystems Inc., Foster City, Calif.) following the manufacturer's protocol.

Synthesis of Peptides

Peptides synthesized by the Merrifield solid phase method (16) were purchased from Chiron Mimotopes (Melbourne, Australia), dissolved in dimethyl sulphoxide and diluted in serum-free RPMI 1640 medium for use in standard CTL assays.

MHC Stabilisation Assays

"To identify the potential HLA A2 binding peptides within LMP1, the HLA Binding Predictions program of the Bioinformnatics & Molecular Analysis Section of the Computational Biosciences and Engineering Lab, Center for Information Technology at the National Institutes for Health, 12 South Drive, MCS 5624 (Building 12A, Room 2033), Bethesda MD 20892, USA, was employed as described elsewhere (18). These predicted peptides were then used in a standard MHC stablization assay using T2 cells as described earlier (1). Briefly, T2 cells ($2\times10^5$) were incubated with 200 $\mu$l of each of the peptides (200 $\mu$g/ml) at 26° C. for 14–16h, followed by incubation at 37° C. for 2–3h. After the incubations, HLA A2 expression was measured by FACS using a monoclonal HLA A2-specific antibody (MA2.1; ATCC).

Generation of Polyclonal and Clonal LMP1-specific CTLs

To generate polyclonal CTLs, PBMC from HLA A2-positive donors were co-cultivated for seven days with the irradiated (8,000 rads) T2 cells sensitized with synthetic peptides. On day 7, these lymphocytes were restimulated with peptide-sensitized T2 cells. After 10 days of culture in growth medium, the cells were used as polyclonal effectors in a standard $^{51}$Cr-release assay against peptide-sensitized autologous PHA blasts.

To generate LMP1-specific CTL clones, PBMC ($10^6$/ml) were cultivated with peptide sensitized autologous lymphocytes (responder to stimulator ratio of 4:1) in 2 ml culture wells (Linbro) for 3 days in growth medium. CTL clones, generated by seeding in 0.35% agarose, were established and maintained in growth medium containing highly purified recombinant human IL-2 from *E. coli* (16), restimulating twice weekly with autologous LCLs. These CTL clones were screened on a panel of recombinant vaccinia-infected autologous CD40 B cells to confirm the antigen specificity (see below).

Vaccinia Virus Recombinants

Recombinant vaccinia constructs encoding EBV latent antigens and a vaccinia virus construct made by insertion of the pSC11 vector alone and negative for thymidine kinase (Vacc.TK-) have been previously described (6.11). CD40 B cells were infected with recombinant vaccinia virus at a multiplicity of infection (MOI) of 10:1 for 1 h at 37° C. as described earlier (6,11). After overnight infection, cells were washed with growth medium and processed for CTL assays or for immunoblotting to assess the expression of recombinant EBV antigens (12).

Cytotoxicity Assay

Target cells were either infected with recombinant vaccinia viruses or pre-sensitized with synthetic peptide epitopes (wild-type or variant) and then incubated with $^{51}$Cr for 90 min. Following incubation, these cells were washed in growth medium and used as targets in a standard 5 h $^{51}$Cr-release assay (16). In some experiments, monoclonal antibodies (MoAb) specific for the non-polymorphic determinants on MHC class I (W6/32) or class II (L243) antigens were added to define the MHC restriction of the CTL clones.

Limiting Dilution Analysis (LDA)

PBMC from HLA A2-positive donors were distributed in graded numbers (two fold dilutions) from $6.25\times103$ to $5\times104$ cells per well in round-bottomed microtiter plates. Approximately $5\times10^4$ K-irradiated (2,000 rads) peptide sensitized (1 $\mu$g/ml) auologous PBMC were added to give a total volume of 100 $\mu$l. Twenty-four replicates were used at each concentration in each experiment. Cultures were fed on days 4 and 7 with 50 $\mu$l of medium supplemented with 20U of rIL-2 and 30% (vol/vol) supernatant from MLA-144 cultures. On day 10, each CTL microculture was split into two replicates and used as effectors in a standard 5 h$^{51}$Cr-release assay against autologous PHA blasts precoated with an LMP1 peptide or left uncoated. Wells were scored as positive when the percent specific chromium release for peptide-sensitized target cells exceeded the mean release from untreated control wells by 3 SDs. LDA was performed by the method of maximum likelihood estimation (4). Data from all experiments were compatible with the hypothesis of single-hit kinetics (P>0.4) and precursor estimates are given with 95% confidence limits.

Results

Identification of HLA A2 Binding Peptides Within LMP1

"To identify potential HLA A2-restricted epitopes within LMPl, the amino acid sequence was analyzed using the HLA Binding Predictions program of the Bioinformatics & Molecular Analysis Section of the Computational Biosciences and Engineering Lab, Center for Information Technology at the National Institutes for Health, 12 South Drive, MCS 5624 (Building 12A, Room 2033), Bethesda Md. 20892, USA (18). A total of 11 peptides with an estimated half-time disassociation score of >400 were selected (Table 1). These peptides were then tested for HLA A2 bindin-efficiency using HLA A2-positive T2 cells. Representative data from a series of experiments is presented in FIG. 1. This analysis showed that six, peptides significantly increased the expression of HLA A2 on T2 cells suggesting that these peptides bind to this allele.

Generation of Polyclonal CTLs Specific for LMP1 Peptides

Figure 2:
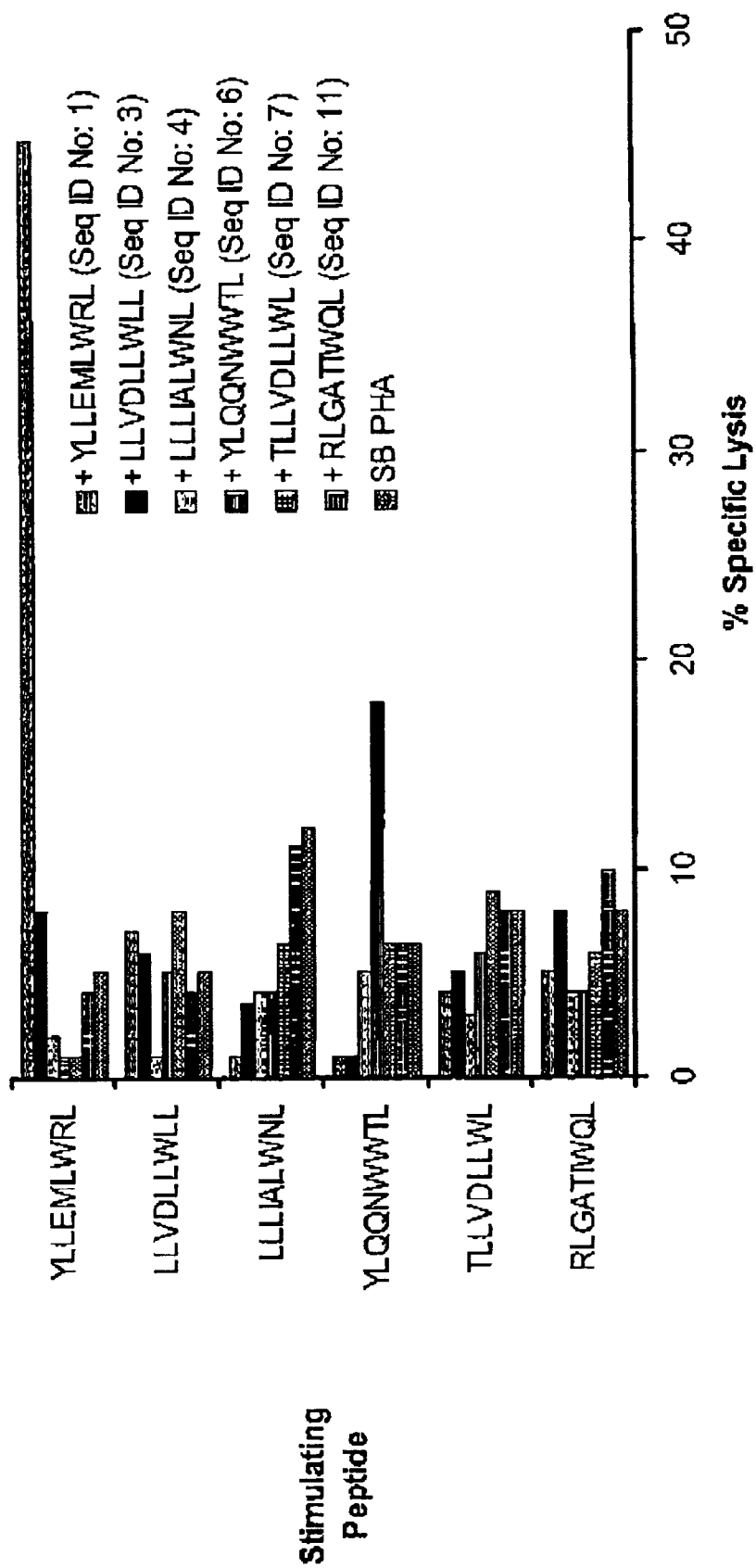
FIG. 2:Recognition of LMP1 peptides by polyclonal CTLs from an HLA A2-positive donor SB. PBNIC from donor SB were co-cultivated for seven days with irradiated T2 cells sensitized with synthetic peptides (indicated on the Y-axis). On day 10, these cells were used as polyclonal effectors in a standard $^{51}$Cr-release assay against peptide-sensitized (1 µg/ml) autologous PHA blasts. An effector:target ratio of 20:1 was used in the assay. Data from one representative experiment out of three is shown. Results are expressed as percent specific lysis.

The data presented above strongly suggested that LUP1 includes sequences which can bind HLA A2 molecules and are therefore potential targets for virus-specific CTLs. To verify this hypothesis, PBMC from two HIA A2-positive EBV immune donors (SB and AS) were stimulated with T2 cells sensitized with each of the HLA A2-binding peptides from LMP1. On day 10, these effector cells were tested against peptide-sensitized autologous PHA blasts. Represtative data from polyclonal CTLs from donor SB are presented in FIG. 2. Two peptides, YLQQNWWTL (SEQ ID NO:6) and YLLEMLWRL (SEQ ID NO:1), showed significant activation of polyclonal CTLs; however, the YLLEMEWRL-stimulated CTLs consistently showed significantly stronger CTL activity when compared to the YLQQNWVVTL-stimulated cells. Similar data were also obtained for another HLA A2-positive donor (AS) (data not shown).

TABLE 1

Identification of Potential HLA A2 Binding Peptides within LMP1*

| Ranking | Residue | Peptide Sequence | Score (Estimate half-time disassociation from HLA A2 allele) |
|---|---|---|---|
| 1 | 125–133 | YLLEMLWRL (SEQ ID NO: 1) | 25714.76 |
| 2 | 32–40 | LLLALLFWL (SEQ ID NO: 2) | 9858.69 |
| 3 | 167–175 | LLVDLLWLL (SEQ ID NO: 3) | 2568.45 |
| 4 | 92–100 | LLLIALWNL (SEQ ID NO: 4) | 2317.87 |
| 5 | 173–181 | WLLLFLAIL (SEQ ID NO: 5) | 1302.88 |
| 6 | 159–167 | YLQQNWWTL (SEQ ID NO: 6) | 1252.90 |
| 7 | 166–174 | TLLVDLLWL (SEQ ID NO: 7) | 999.86 |
| 8 | 171–179 | LLWLLLFLA (SEQ ID NO: 8) | 935.11 |
| 9 | 152–160 | ILLIIALYL (SEQ ID NO: 9) | 739.03 |
| 10 | 110–118 | VLFIFGCLL (SEQ ID NO: 10) | 510.60 |
| 11 | 132–140 | RLGATIWQL (SEQ ID NO: 11) | 441.60 |

*To identify the potential HLA A2 binding peptides within LMP1, the HLA Binding Predictions program of the Bioinformatics & Molecular Analysis Section of the Computational Bioscience and Engineering Lab, Center for Information Technology at the National Institutes for Health, 12 South Drive, MCS 5624 (Building 12A, Room 2033), Bethesda MD 20892, USA, was employed as described elsewhere (18). This program can be directly accessed through the world-wide web.

Charaterization of LMP1 CTL epitope

Figure 3A:
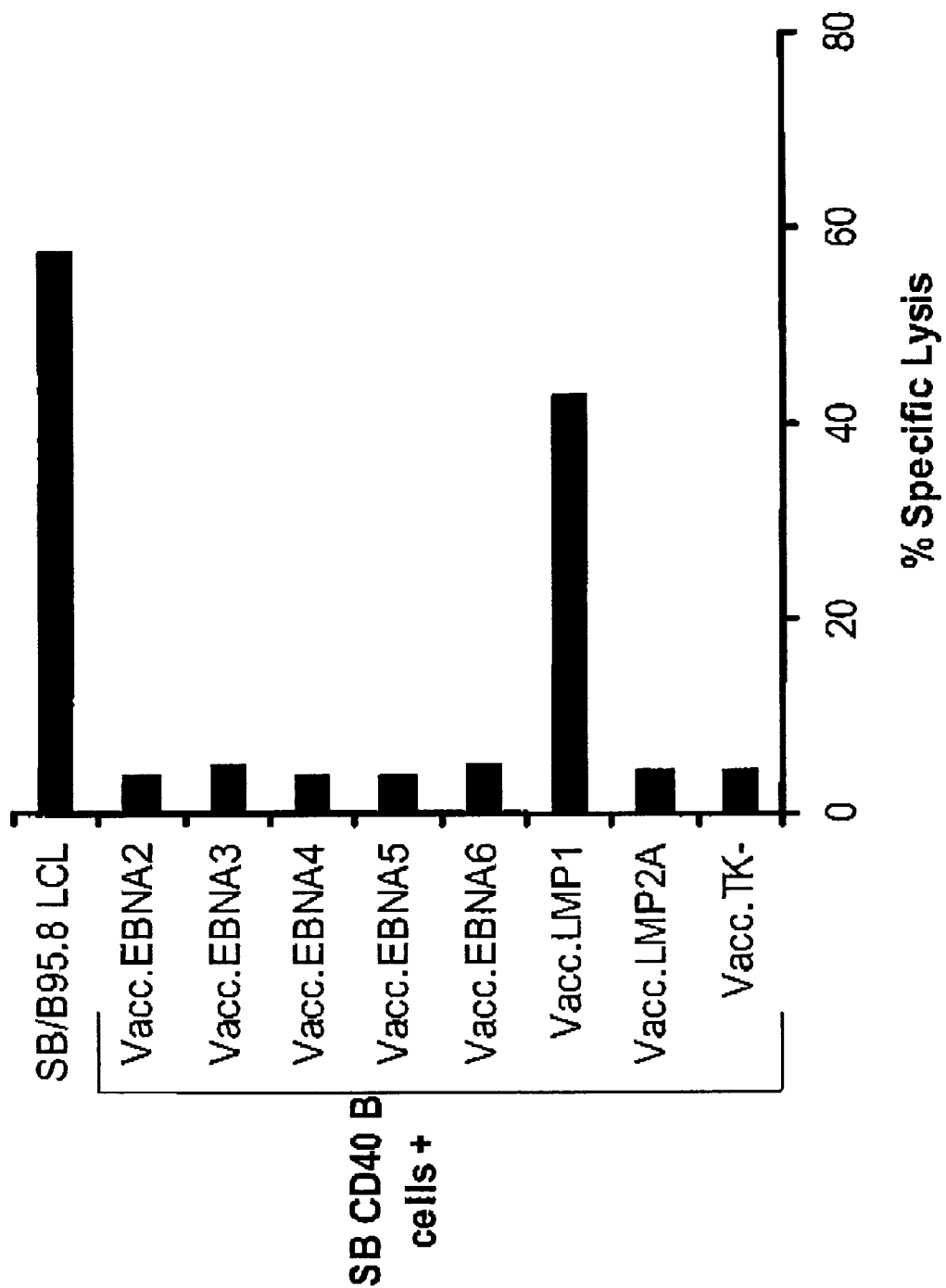
FIG. 3:Specific lysis by an EBV-specific CTL clone (SB7) from donor SB of autologous LCLs and autologous CD40 B cells infected with Vacc.EBNA1, 2, 3, 4, 5, 6, LMP1, LKP2A and Vacc.TK-(panel A). Target cells were infected for 12–14 h (M.O.I=10:1) with vaccinia constructs and processed for the standard $^{51}$Cr-release assay. Vacc.TK- was used as a control recombinant vaccinia. To further confirm the LMP1 specificity of the SB7 clone, LMP11-and HLA A2-positive BL cell lines (BJAB. MTLM6 or Mutu cl.59) and LMP1-negative, HLA A2-positive BL cell lines (BJAB.gpt1 and Mutu cl.216) were used as targets in a standard $^{51}$Cr-release assay (panel B). An effector:target ratio of 4:1 was used in both assays. Results are expressed as percent specific lysis.
Figure 3B:
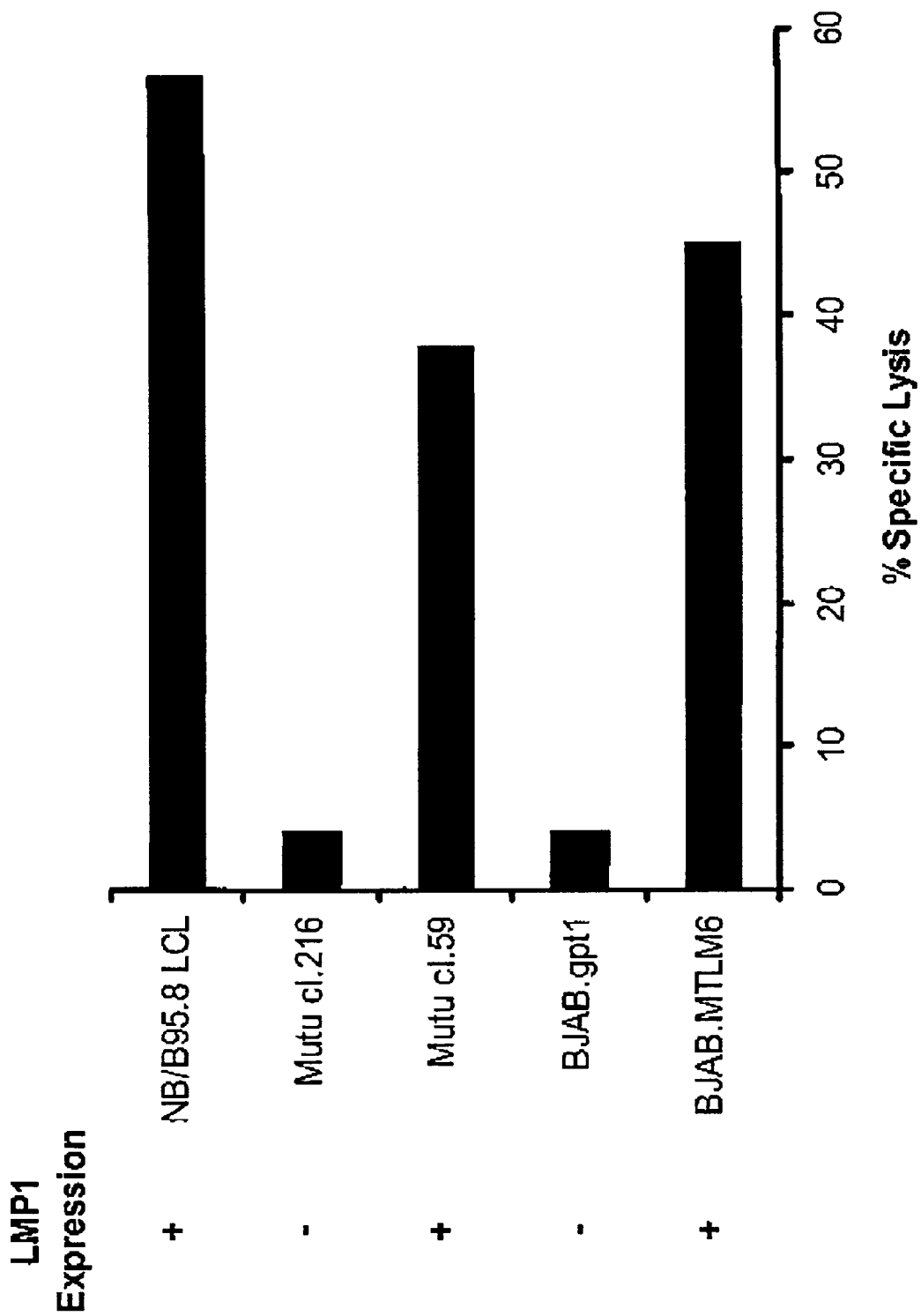

To further characterize the CTL epitopes identified by the polyclonal CTLs, vinis-specific CTL clones were generated using initial stimulation with peptide sensitized autologous PBNIC followed by continous restimulation with irradiated autologous LCLs. Proliferating clones were screened for peptide recognition using the rapid visual assay for CTL specificity (2) and one clone, SB7, clearly recognized the YLLEMLWRL (SEQ ID NO:1) peptide. No CTL clones specific for YLQQNWWTL (SEQ ID NO:6) were isolated using this procedure. To further confirm the antigen specificity of the SB7 clone, autologous CD40-stimulated B cells were infected with recombinant vaccinia viruses encoding individual EBV antigens and then exposed to these CTLs. The data presented in FIG. 3A clearly demonstrate that only target cells infected with the LMP1-expressing vaccinia construct were recognized. In addition, only LMP1- and HLA A2-positive BL cell lines (BJAB.MTLM16 or Mutu cl.59) were efficiently lysed by this clone, while BL cells negative for this antigen (BJAB.gpt1 and Mutu cl.216) were not recognized (FIG. 3B). These results confirm that YLLELWRL (SEQ;ID NO:1) is an LMP1 CTL epitope that is endogenously processed by virus-infected cells.

Figure 4A:
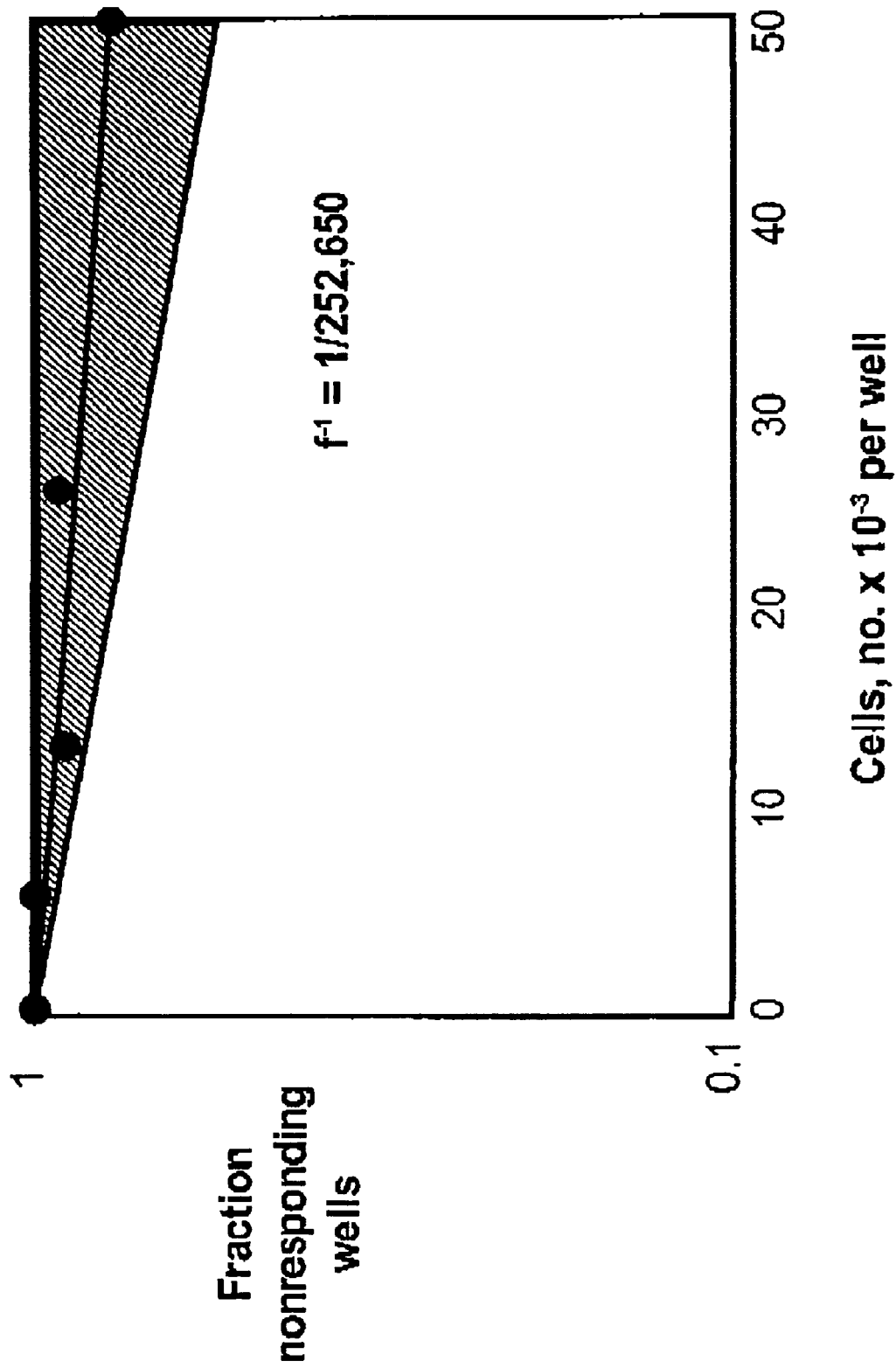
FIG. 4:CTLp frequencies for the LMIP1 epitopes YLQQNWWTL (SEQ ID NO:6) (A) and YLLEMLWRL (SEQ ID NO:1) (B) in HLA A2-positive donor are shown. Using limiting dilution analysis, the frequencies of CTLp for peptides YLQQNWWTL (SEQ ID NO:6) (A) and YLLEMLWRL (SEQ ID NO:1) (B) were estimated in peripheral blood lymphocytes from donor SB. PBNFC from this donor was stimulated with peptides sensitized PBNIC as described in the "Niaterials and Niethods" section. Reciprocal values of responder frequencies (f$^1$) are indicated. The shaded areas indicate 95% confidence limits.
Figure 4B:
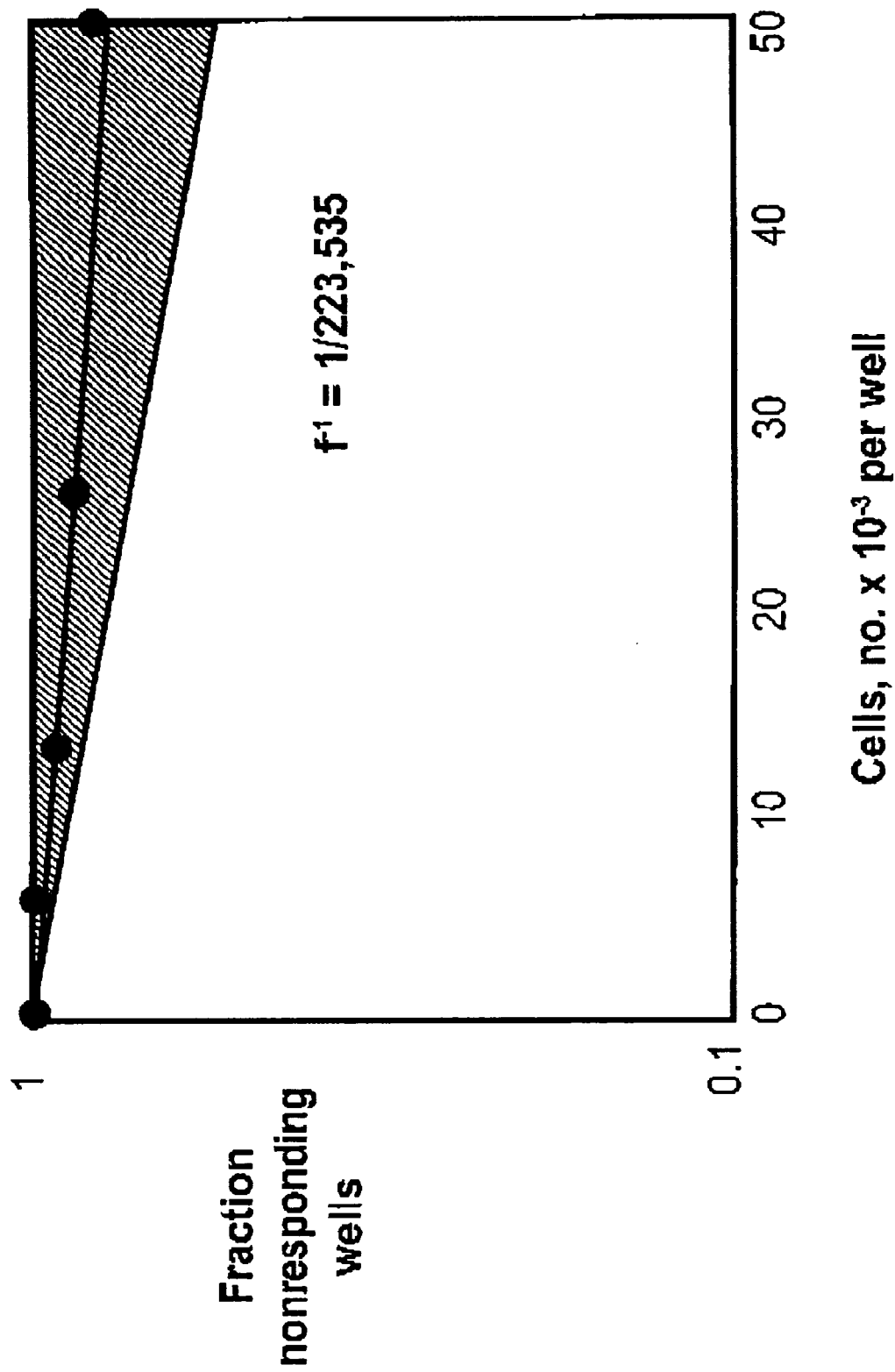

In the next set of experiments we analyzed the frequency of CTL precursors (CTLp) for this epitope in PBMC from HLA A2-positive healthy EBV immune donors by limiting dilution analysis. YLLEMLWRL-specific CTLp were reactivated in vitro by stimulation of PBMCs from donors SB and AS with autologous peptide-sensitized PBMCs. Autologous PHA blasts precoated with peptide YLLEMLWRL (SEQ ID NO:1) or untreated were used as target cells in a chromium release assay. The representative data in FIG. 4 show that a very low frequency of memory CTL specific for the YLLEMELWRL (SEQ ID NO:1) epitope were detected in the HLA A2:positive donors AS (1:223,535+/−107,437) and SB (1:252,650+/−122,875).

Figure 5:
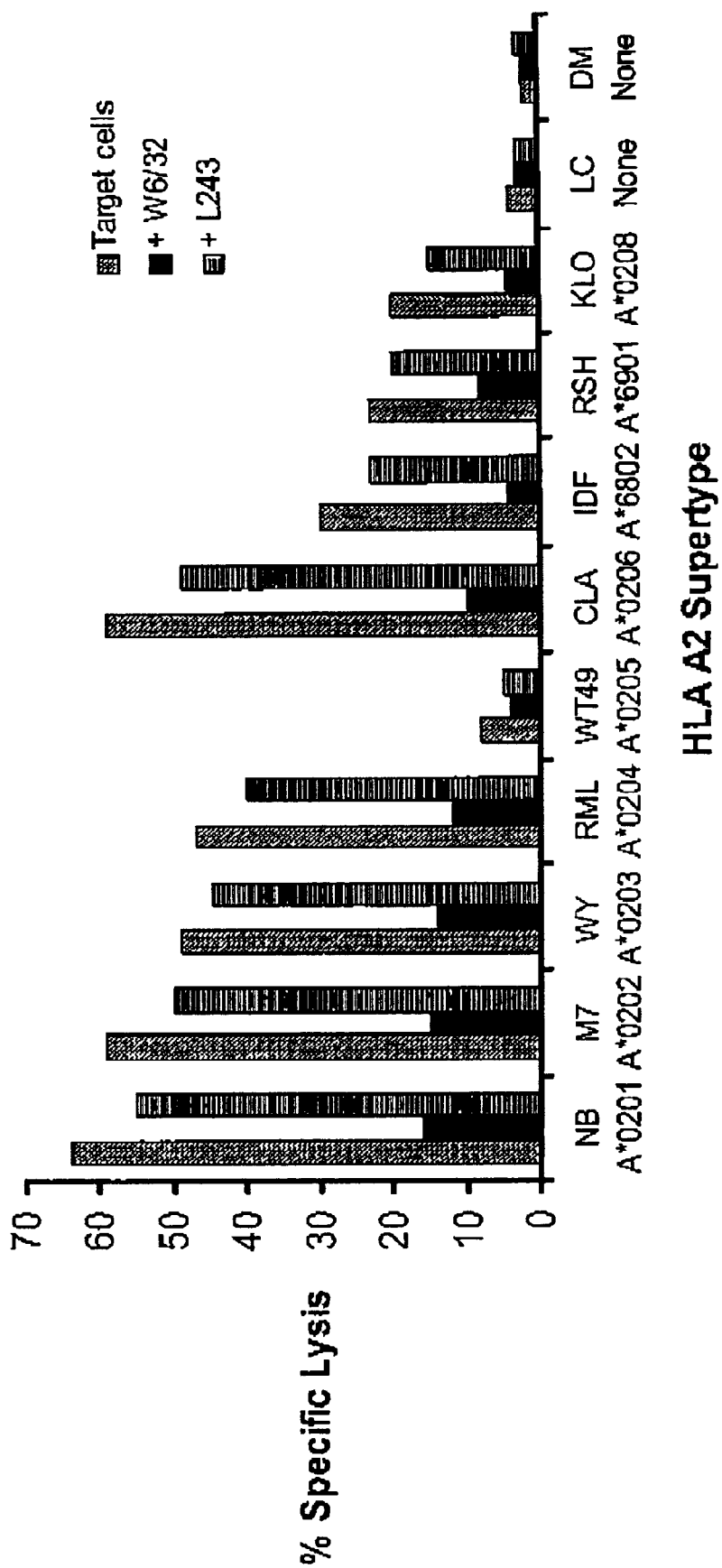
FIG. 5:CTL recognition of LCLs expressing different supertypes of HLA A2 by the SB7 CTL clone. All LCLs used in this assay were transformed with the B95.8 EBV isolate. The HLA A2 subtyping for each LCL was assigned by the 12th Histoconmpatability workshop. An effector:target ratio of 4:1 was used in both the assay. Results are expressed as percent specific lysis. Data from one representative experiment out of four is shown.

To determine whether EBV-transformed LCLs expressing different HLA A2 supertypes could be recognized by clone SB7, a panel of LCLs expressing ten different supertypes of the HLA A2 allele (HLA A*0201-HLA A*0210) were screened in a standard CTL assay. The data presented in FIG. 5 clearly demonstrate that LCLs expressing all the major HLA A2 supertypes except HLA A*0205 were efficiently recognized by the CTL clone SB7. This lysis was significantly inhibited by the HLA class I-specific antibody W6/32. Surprisingly, HLA A2-positive and TAP-negative T2 cells were also recognized by this clone suggesting that the YLLEMLWRL (SEQ ID NO:1) epitope is endogenously processed through a TAP-independent pathway (FIG. 5).

Sequence Analysis of the HLA A2-Restricted LMP1 Epitope in Virus Isolates from NPC Patients and Healthy Donors Efficient presentation of the LMP1 epitope by H A*0201, HLA A*0203 and HIA A*0207, which are common supertypes in the Southeast Asian ethnic population, raised the possibility that this epitope might be important as a potential target epitope for LMP1-expressing NPC. Sequence analysis across this CTL epitope region in virus isolates from eight NPC samples was carried out using LMP1-specific primers. Spontaneous LCLs from healthy EBV immune donors were used as controls in this analysis. Interestingly all EBV isolates from the NPC samples displayed identical substitutions within this epitope (Table 2).

In contrast, of the 12 virus isolates from healthy EBV immune donors, four encoded a sequence identical to that of the B95.8 isolate, while six displayed a different pattern of alterations within this epitope that differed from those found in the NPC samples. In some isolates leucine at position 2, methionine at position 5 and arginine at position 8 were substituted with phenylalanine, isoleucine and glycine, respectively (Table 2), while in other isolates only the methionine at position 5 was substituted with isoleucine.

Figure 6A:
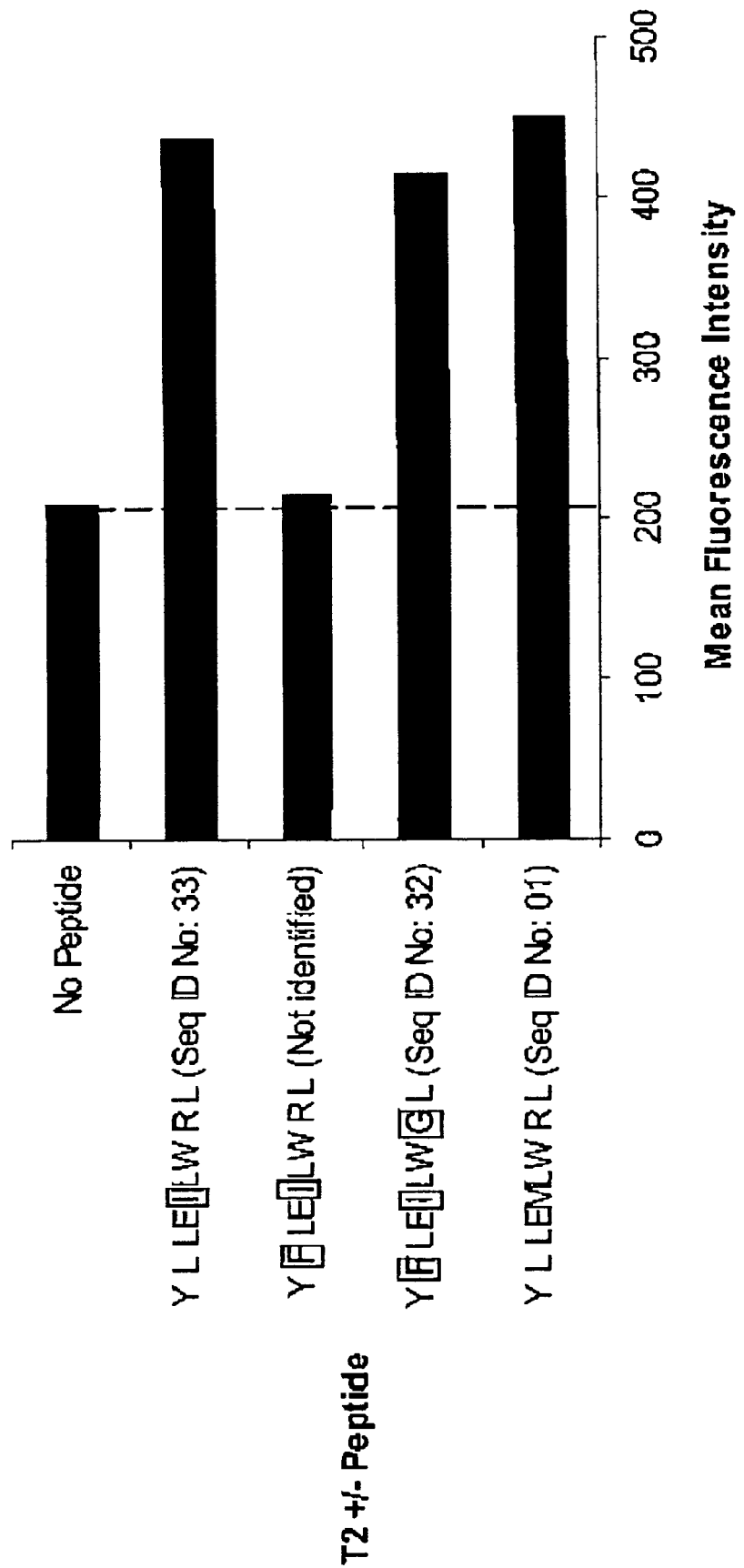
FIG. 6:Effect of variant LMP1 peptides on the HLA A2 binding (panel A) and CTL recognition (panel B). For HLA A2 binding analysis on T2 cells were initially incubated with 200 µl of each of the peptides (200 µg/ml) for 14–16h at 26° C. followed by incubation at 37° C. for 2–3h. HLA A2 expression on these cells was analysed by FACS using BB7.2 antibody (panel A). The dotted line indicates the background mean fluorescence intensity for HLA A2 on T2 cells without any peptide. For CTL recognition of the variant and prototypic HLA A2-restricted LMP1 epitope. PHA blasts from donor SB were sensitized with serial dilutions of each of the peptides and then exposed to the SB7 CTL clone (panel B) at an effector:target ratio of 4:1. Results are expressed as percent specific lysis. Data from one representative experiment out of three is shown. Amino acid changes in the variant peptides are indicated by bold letters.
Figure 6B:
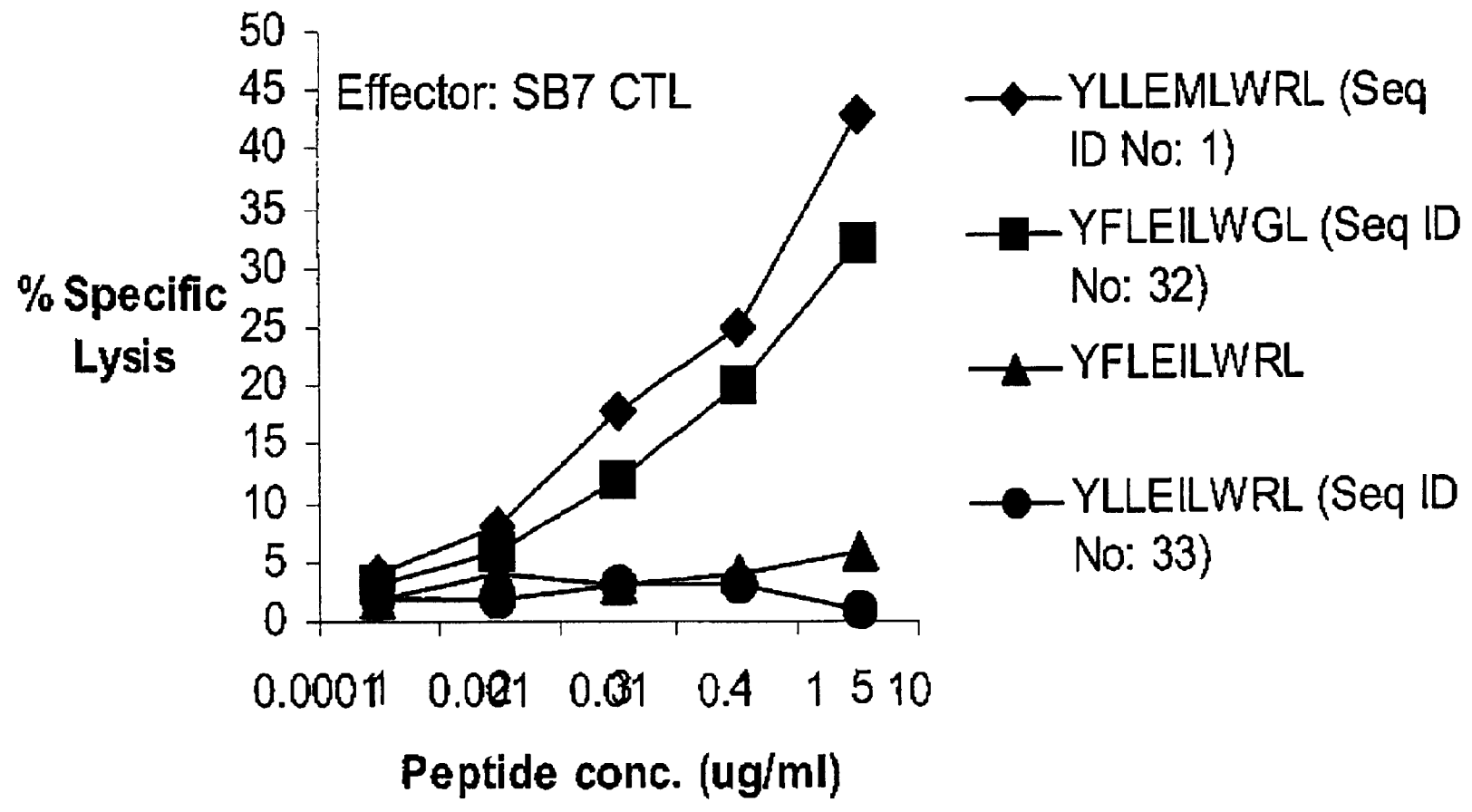
Figure 7A:
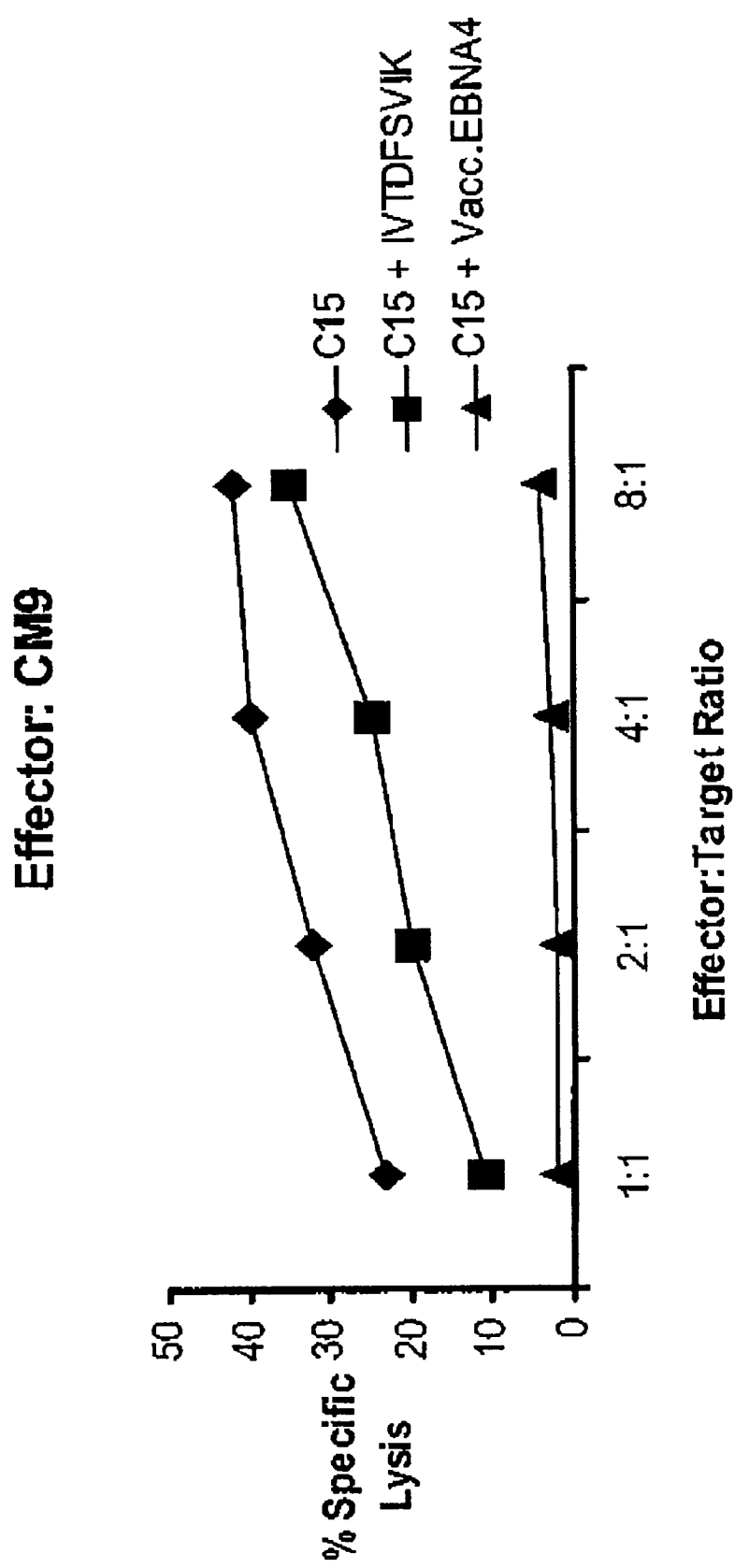
FIG. 7:CTL recognition of NPC cells and LCLs by EBV-specific HLA A11-restricted CTL clones CM9 (a & c) and CM29 (b & d). Vacc.EBNA4, Vacc.TK infected or peptide sensitized C15NPC cells (a & b) were exposed to CTL clones at different effector to target ratios and the level of CTL lysis was compared to a type 2 LCLs (CM/A/Ag876 LCL). As a positive control, target cells were either presensitized with IVTDFSVIK peptide (a & c), or AVFDRKSDAK peptide (b & d). The results were expressed as per cent specific lysis.
Figure 7B:
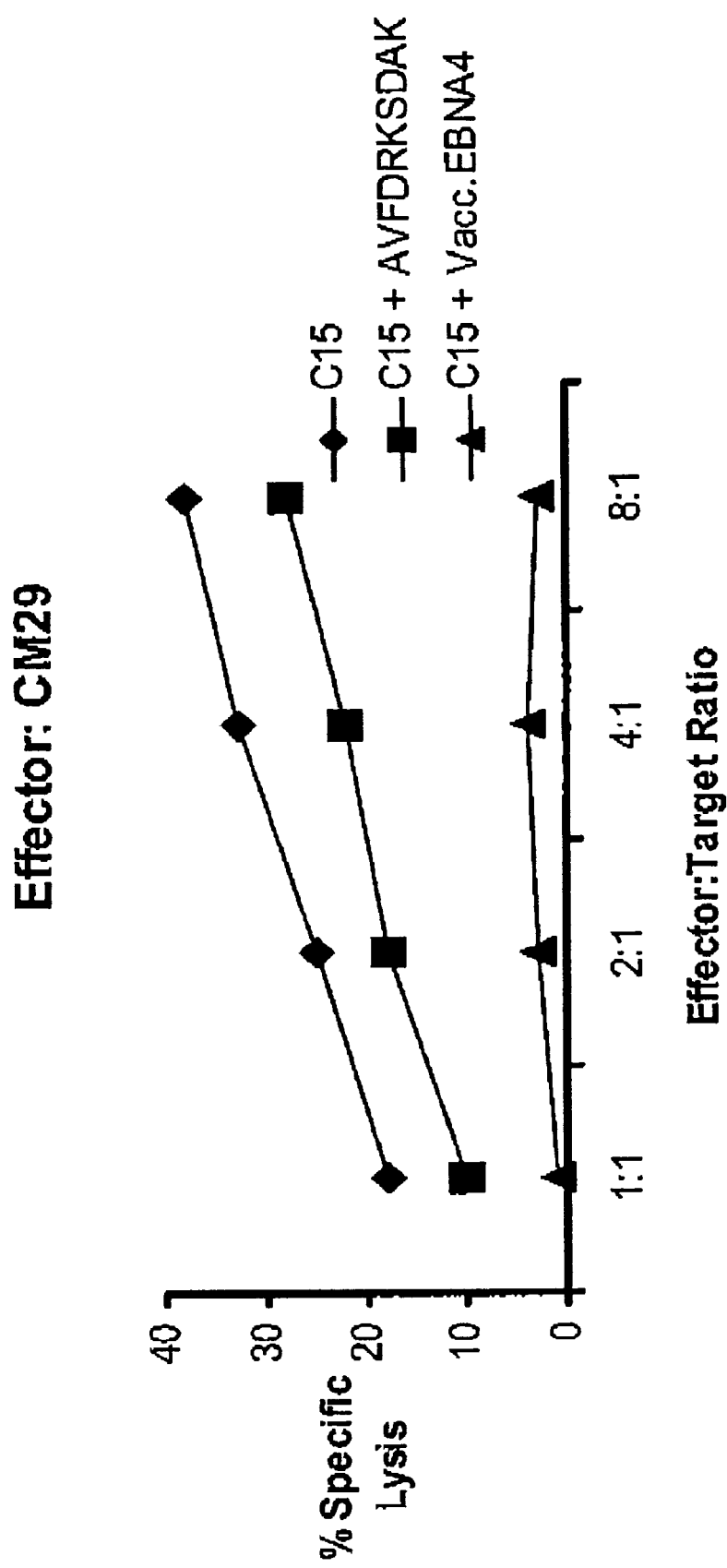
Figure 7C:
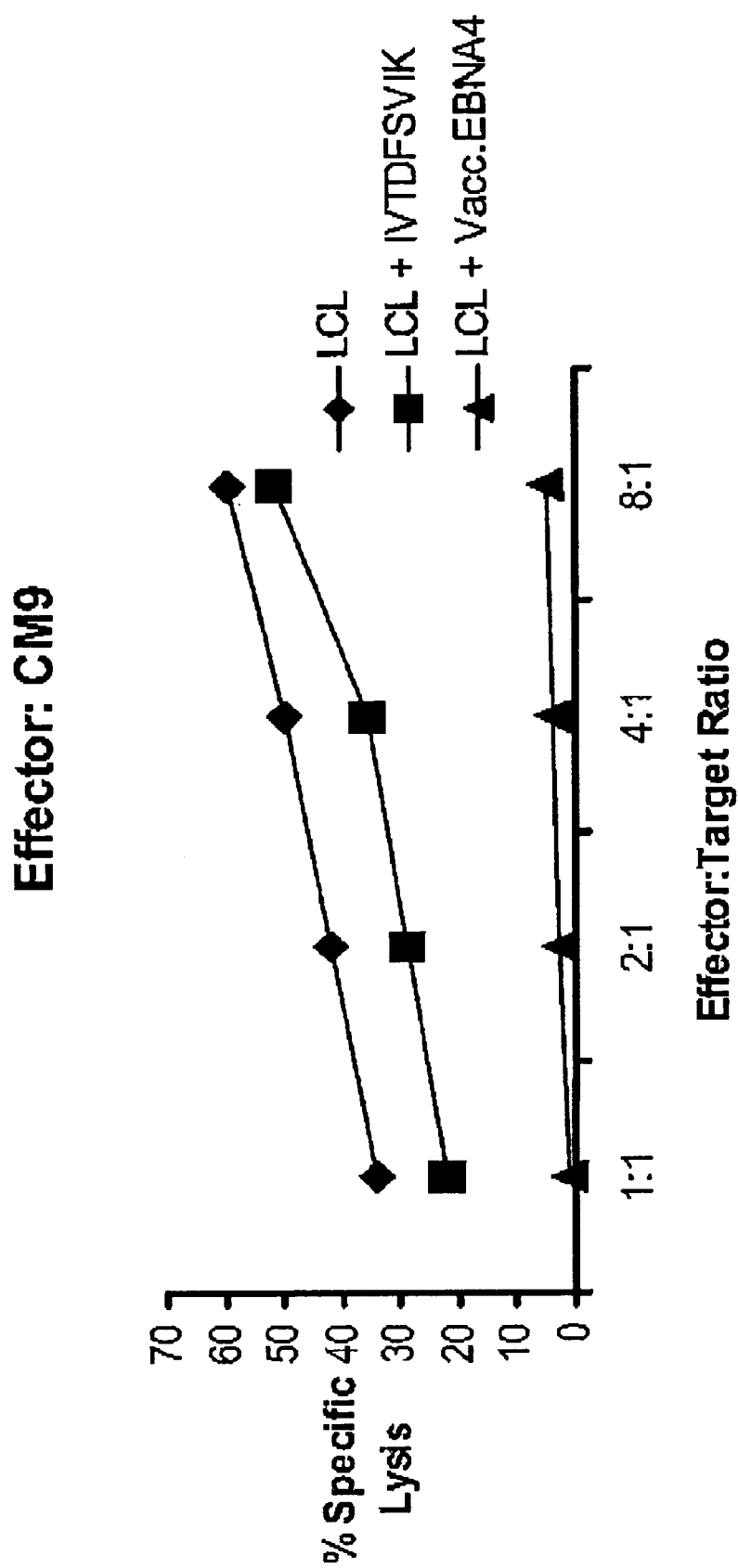
Figure 7D:
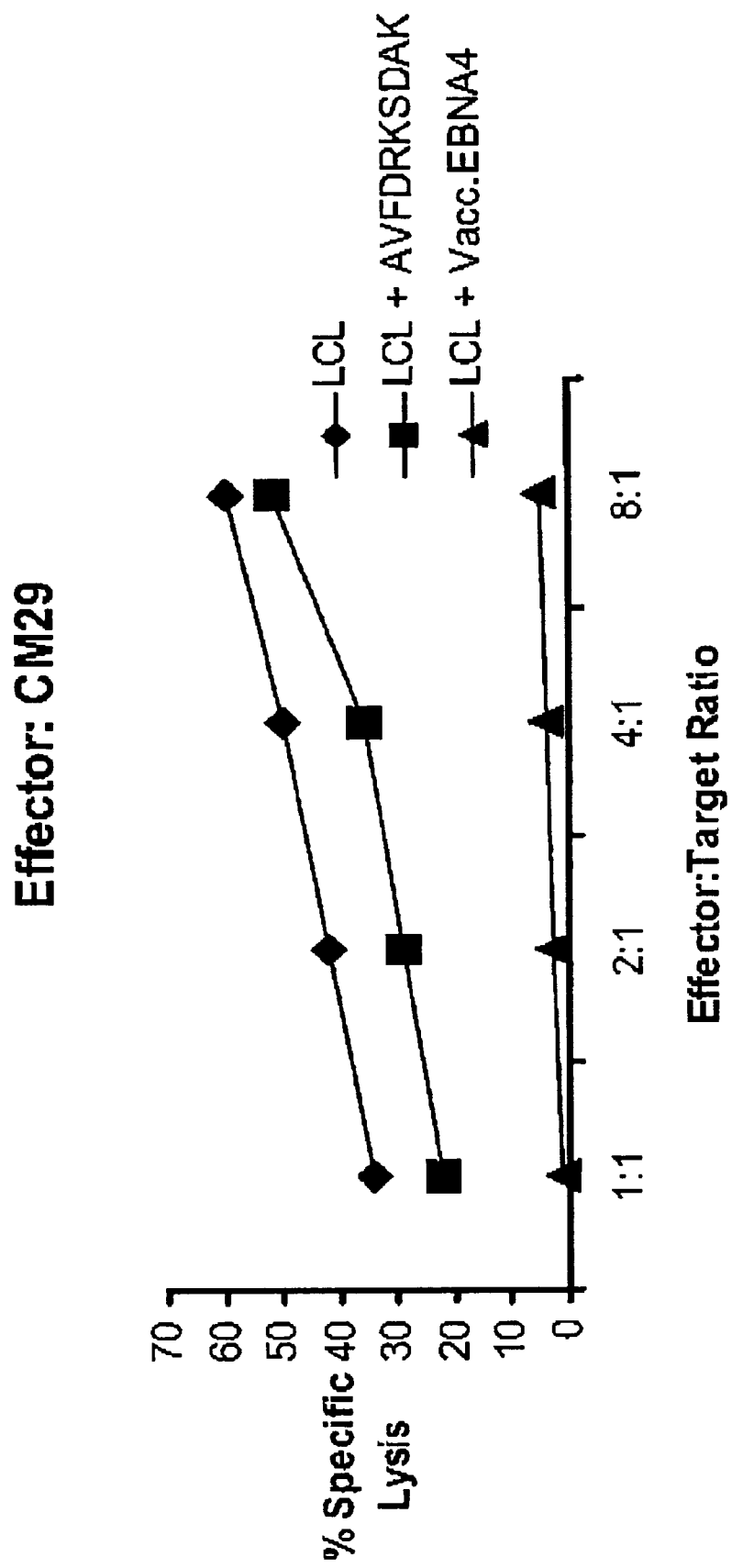

Importantly, incubation of T2 cells with these variant peptides (YFLEILWGL (SEQ ID NO:32) and YLLEILWRL (SEQ ID NO:33)) significantly increased IHC expression on these cells (FIG. 6A), indicating efficient binding to HLA A2, the YLLEILWRL (SEQ ID NO:33) peptide was efficiently recognized by the SB7 clone, while no CTL activity was seen in the presence of the YFLEILWGL (SEQ ID NO:32) peptide (FIG. 6B). The latter result does not rule out the possibility that YFLEILWGL (SEQ ID NO:32) is an epitope individuals infected with an EBV strain encoding this sequence. The loss of recognition by the clone SB7 is likely to be due an inappropriate T cell receptor interaction with the MHC-peptide complex rather than loss of MHC binding. Thus it is possible that T cells expressing a different T cell receptors are capable of efficiently recognising this HLA binding peptide (8). Interestingly, virus isolates from the other two healthy EBV immune donors

TABLE 2

Sequence of HLA A2-restricted LMP1 epitope (YLLEMLWRL) in EBV isolates from NPC and healthy seropositive individuals.

| Virus | Origin | Epitope Sequence[a] | HLA A2[b] Binding | Number of Isolates |
|---|---|---|---|---|
| B95.8 | | $^{96676}$TAC TTA TTG GAG ATG CTC TGG CGA CTT$^{96702}$<br>Y    L    L    E    M    L    W    R | ++++ | |
| NPC | Southeast Asia | --- --C --- --- --T --- --- --- ---<br>-   F   -   -   I   -   -   -   - | - | 8 |
| Healthy donors | Caucasian | --- --- --- --- --- --- --- --- ---<br>-   -   -   -   -   -   -   -   - | ++++ | 4 |
| | Caucasian | --- --- --- --- --T --- --- --- ---<br>-   -   -   -   I   -   -   -   - | ++++ | 2 |
| | Caucasian | --- --C --- --- --T --- --- G-G ---<br>-   F   -   -   I   -   -   G   - | ++++ | 4 |
| | Caucasian | --- --C --- --- --T --- --- --- ---<br>-   F   -   -   I   -   -   -   - | - | 1 |

TABLE 2-continued

Sequence of HLA A2-restricted LMP1 epitope (YLLEMLWRL) in EBV isolates
from NPC and healthy seropositive individuals.

| Virus | Origin | Epitope Sequence[a] | HLA A2[b] Binding | Number of Isolates |
|---|---|---|---|---|
| | Southeast Asia | --- --C --- --- --T --- --- --- --- <br> - F - - I - - - - | – | 1 |

[a]Oligonucleotide primers used for PCR amplification were (YLL1:CTTCGGGTGCTTACTTGGTA; YLL2: TCATCGTGGTGGTGTTCA 3')
[b]HLA A2 binding data is adapted from FIG. 6. ++++ indicates strong binding; – indicates no binding (including one from Southeast Asia) displayed changes within the epitope sequence which were identical to those seen in the NPC samples (Table 2).

Analysis of Antigen Processing Function of NPC cells

To determine whether NPC cells can present endogenously expressed antigens to virus-specific CTLs, tumour cells were either infected with recombinant vaccinia encoding EBNA4 (Vacc.EBNA4) or presensitized with synthetic peptide epitopes. FIG. 7 illustrates the results from an experiment in which recombinant vaccinia-infected NPC cells (Cl5) were compared with HLA-matched type 2 LCLs infected with Vacc.EBNA4. Following exposure to EBNA4-specific CTLs, Vacc.EBNA4-infected or peptide sensitized NPC cells were efficiently recognised by both CM9 and CM29 CTL clones. The level of CTL lysis was comparable to that seen for LCLs. These results clearly demonstrate that NPC cells are able to transport sufficient levels of peptides into the ER by TAP-dependent mechanism and can efficiently transport MHC-peptide complexes from the ER to the surface of the cell.

Normal antigen processing function in NPC cells has significant implications for vaccines designed to control these tumours in vivo. Earlier studies have demonstrated that the latent gene expression in NPC is often limited to EBNA1 and the transmembrane proteins, LMP1 and LMP2 (29).

Since EBNA1 is not recognized by EBV-specific CTLs, there is an increasing emphasis on designing strategies to control NPC around epitopes known to be included within LMP1 (6,17). In view of the data presented in this study, it is reasonable to assume that LMP epitopes will be processed efficiently by NPC cells. An effective approach to control NPC cells in vivo may be to amplify LMP-specific CTL responses in these patients. This might be achieved by two different procedures. Firstly NPC patients might be immunised with synthetic peptides which include CTL epitopes from LMP1 and/or LMP2. Alternatively. LMP1 and LMP2-specific CTLs from HLA matched healthy virus carriers may be adoptively transferred into NPC patients in a manner analogous to that used to successfully treat EBV-associated polyclonal lymphomas in bone marrow transplant recipients (30).

Discussion

Earlier work from various laboratories have shown that the viral phenotype of EBV-associated malignancies is likely to be a very important factor in reducing tumor susceptibility to virus-specific CTL surveillance, since viral antigen expression in these malignant cells in vivo is restricted to either EBNA1, or EBNA1 and LMP1 (9,20,21). Since it is now firmly established that EBNA1 does not include class I-restricted CTL epitopes (6,17), considerable interest has been directed towards identifying potential epitopes within LMP1. The present study was precisely designed to, address this issue. One of the limiting factors in identifying epitopes within LMP1 has been the fact that the CTL response to this antigen often constitutes as a minor component of the total virus-specific response (6,17). To overcome this problem we employed a modified protocol to identify potential HLA A2-restricted epitopes within LMP1. An important step in this process was the use of a computer based program developed by Parker and colleagues (18) designed to predict the potential HLA binding peptides within various proteins from human pathogens. Analysis of the LMP1 sequence from the B95.8 EBV isolate revealed a number of potential HLA A2 binding peptides and a large proportion of these were then functionally shown to stabilize HLA A2 molecules on T2 cells. Stimulation of PBMCs with these peptides resulted in the activation of a strong polyclonal CTL response specific for the peptide YLLEMLWRL (SEQ ID NO:1), while a weaker response was seen for another peptide YLQQNWWTL (SEQ ID NO:6). The YLLEMLWRL (SEQ ID NO:1) sequence was confirmed as an LMP1 epitope by isolating a CTL clone (SB7) specific for this peptide. The LMP1 specificity of the SB7 CTL clone was further confirmed by the recombinant vaccinia experiments and efficient lysis of LMP1 expressing H A2-positive BL cells.

The CTL response characterized in the present report is of interest not only because it is directed against a viral antigen constitutively expressed in many EBV-associated malignancies (HD and NPC) but also because the HIA A2 allele is common in virtually all human populations (13). Niore importantly, EBV transformed LCLs expressing all the major HLA A2 supertypes were efficiently recognized by the LMP1-specific CTL clone, a result that has important implications for anti-viral vaccine design aimed at protect different ethnic populations. It is important to mention here that the CTL response to the LMPI epitope in healthy seropositive individuals constitutes a minor component of the virus-specific CTL response and very low levels of CTL precursors are seen for this epitope. It may nevertheless be possible to amplify this component by vaccination with the relevant peptide or with adoptive transfer of in vitro activated LMP1-specific CTLs. Such approaches may be of use in the control of HD and NPC.

Efficient presentation of the YLLEMILWRL (SEQ ID NO:1) peptide by HLA A*0201, HLA A*0203 and HLA A*0207-positive LCLs, which are common supertypes in the southeast Asian population, raises the possibility that this epitope might be exploited as a potential target epitope for LMP1-expressing NPC.

EXAMPLE 2

Materials and Methods

Infectious Mononcleosis (IM) Patients

IM patients, identified on clinical grounds and by heterophile antibody positivity, were bled during the first 5–10 days of illness and, in two cases, on a second occasion 24–36 months after the resolution of symptoms. These patients were HIA typed for the HLA A2 allele by serotyping in microcytotoxicity and by genotyping. Three patients (SB, LP and MG) were identified as HIA A2-positive patients and this was subsequently confirmed by FACS analysis using an HLA A2-specific monoclonal antibody (ATCC). Establishment and Maintenance of Cell Lines:

EBV-transformed lymphoblastoid cell lines (LCLs) were established from a panel of IM and healthy EBV-seropositive donors by exogenous virus transformation of peripheral B cells using type 1 (B95.8) or type 2 (Ag876) EBV isolates (16), and were routinely maintained in RPMI 1640 containing 2 mM glutamine. 100 µg/ml penicillin and 100 µg/ml streptomycin plus 10% foetal calf serum (FCS) (growth medium). In addition, the peptide transporter (TAP)-negative B×T hybrid cell line 174×CEM.T2 (referred to as T2) (22) were used for peptide stablization assays.

To generate phytohaemagglutinin (PHA) blasts peripheral blood mononuclear cells (PBMC) were stimulated with PHA (Commonwealth Serum Laboratories, Melbourne) and after 3 days, growth medium containing MLA 144 supernatant and rIL-2 was added (36). PHA blasts were propagated with bi-weekly replacement of IL-2 and NILA supernatant (no further PHA added) for up to 6 weeks.

Establishment and Preparation of CTL Effectors

Acute IM PBMC effectors for use in ex vivo cytotoxicity assays were resuspended in growth medium supplemented with recombinant IL2 and used directly in a cytotoxicity assay (see below). To generate polyclonal CTLs, PBMCs from HLA A2-positive donors were co-cultivated for seven days with irradiated (8,000 rads) T2 cells presensitized with synthetic peptides (37). On days 7 and 14, these cultures were restimulated with peptide-sensitized T2 cells. After 18 days of culture in growth medium, the cells were used as polyclonal effectors in a standard 51Cr-release assay against peptide-sensitized autologous PHA blasts.

Synthesis of Peptides

Peptides, synthesized by the Merrifield solid phase method! were purchased from Chiron Mimotopes (Melbourne, Australia), dissolved in dimethyl sulphoxide, and diluted in serum-free RPMI 1640 medium for use in standard CTL assays.

MHC Stabilisation Assays HLA A2 binding peptides within the gp85 and gp350 antigens were identified using a protocol as described in Example 1. These predicted peptides were then used in a standard MHC stablization assay using T2 cells. Briefly, T2 cells ($2 \times 10^5$) were incubated with 200 µl of each of the peptides (200 µg/ml) at 26° C. for 14–16h, followed by incubation at 370° C. for 2–3h. After the incubations. HLA A2 expression was measured by FACS using a monoclonal HLA A2-specific antibody (MA2.1:ATCC).

Vaccinia Virus Recombinants

Recombinant vaccinia constructs encoding the EBV structural antigens gp350 (Vacc.gp350) and gp85 (Vacc.gp85), and a vaccinia virus construct made by insertion of the pSC11 vector alone and negative for thymidine kinase (Vacc.TK-) have been previously described (38). Target cells were infected with recombinant vaccinia virus at a mutiplicity of infection (MOI) of 10:1 for 1 h at 37° C., as described earlier (6,12). After overnight infection, cells were washed with growth medium and processed for CTL assays or for immunoblotting to assess the expression of recombinant EBV antigens (11).

Cytotoxicity Assay

Target cells were either infected with recombinant vaccinia viruses or pre-sensitized with synthetic peptide epitopes and then incubated with 51Cr for 90 min. Following incubation, these cells were washed in growth medium and used as targets in a standard 5 h 51Cr-release assay (16).

Immunisation of HLA A2/Kb transgenic mice with gp350 and gp85 CTL epitopes

HIA A2/K b transgenic mice used in this study have been described elsewhere (39). These mice express a chimeric class I molecule composed of the alpha 1 & 2 domains of the human A*0201 allele and the alpha 3 domains of the mouse H-2Kb class I molecules. Peptide immunizations were carried out as described by Vitello and colleagues (40). Briefy, these animals were twice immunized (at a 14 day interval) subcutaneously with 50 µg/mouse of CTL epitopes emulsified in IFA together with 5 µg of Tetanus Toxoid as a source of help. Four weeks following peptide immunization, animals were assessed for gp350- and gp85-specific CTL response. For assessing these CTL responses, splenocytes ($3 \times 10^6$ cells/ml) were cocultured with syngeneic irradiated (2000 rad) peptide-coated LPS blasts ($3 \times 10$ cells/ml) and 3ug/ml human B2-microglobulin. CTL activity was tested on day 6 using a standard 51Cr-release assay.

Vaccinia Protection Assay

For protection experiments, groups of 8 weeks old female A2/Kb transgenic mice were immunized with CTL epitopes as described above. On day 28, mice were challenged with Vacc.gp85 and Vacc.gp350 intraperitonealy ($1 \times 10^7$ pfu in 100 µl PBS). After four days of challenge, these animals were sacrificed and vaccinia titres measured in both ovaries by plaque assay on confluent CV1 cells.

Results

Identification of HLA A2 Binding Peptides Within gp85 and gp350

Figure 8A:
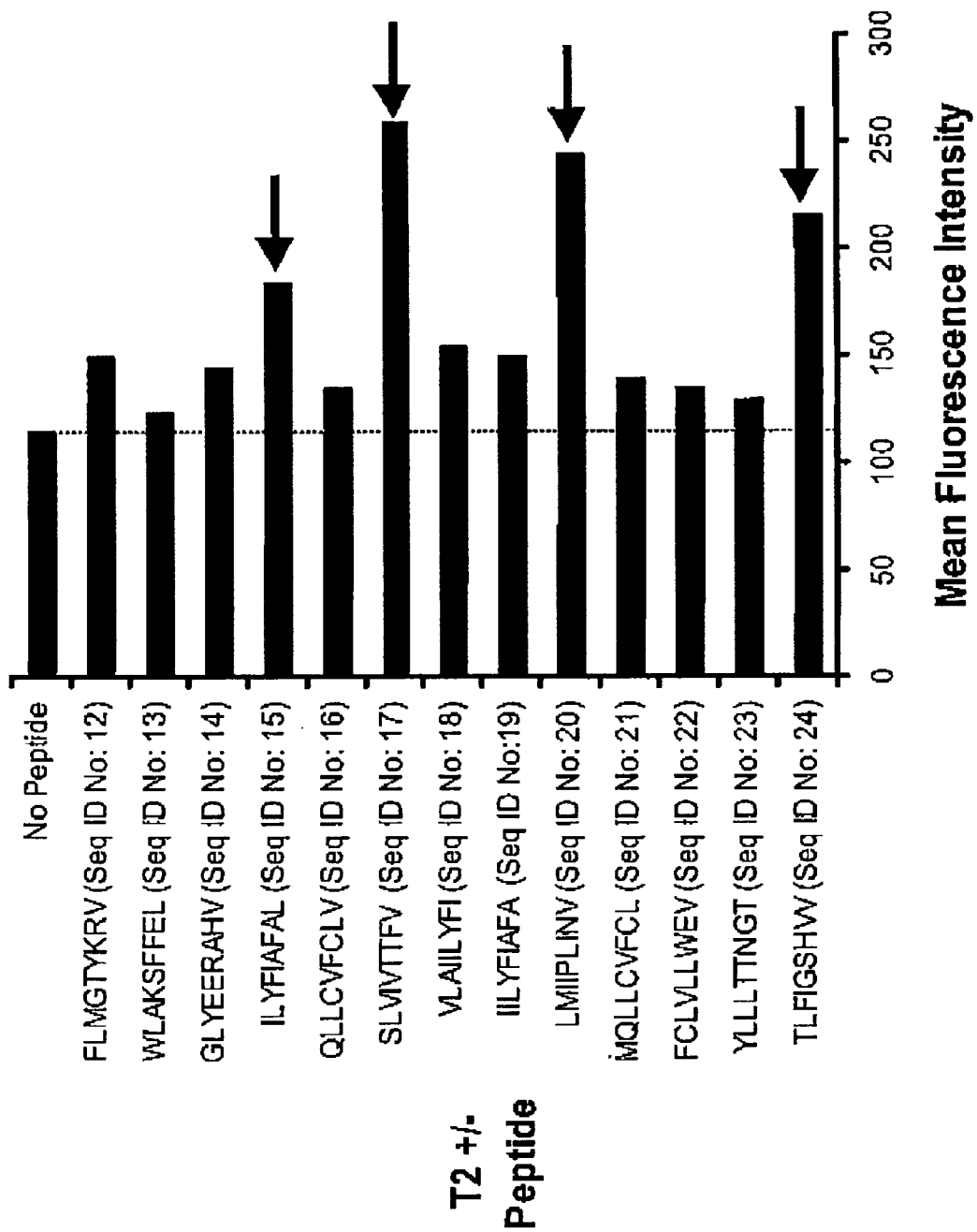
FIG. 8:MHC stabilization analysis on T2 cells using potential HLA A2 binding peptides within gp85 (panel A) and gp350 (panel B). T2 cells were initially incubated with 200Tl of each of the peptides (200Tg/ml) for 14–16h at 26° C. followed by incubation at 37° C. for 2–3h. HLA A2 expression on these cells was analysed by FACS using the BB7.2 antibody. The dotted line indicates the background mean fluorescence intensity for HLA A2 on T2 cells without any peptide. The gp85 and gp350 peptides showing significant stabilization of HLA A2 molecules on T2 cells are indicated by arrows.
Figure 8B:
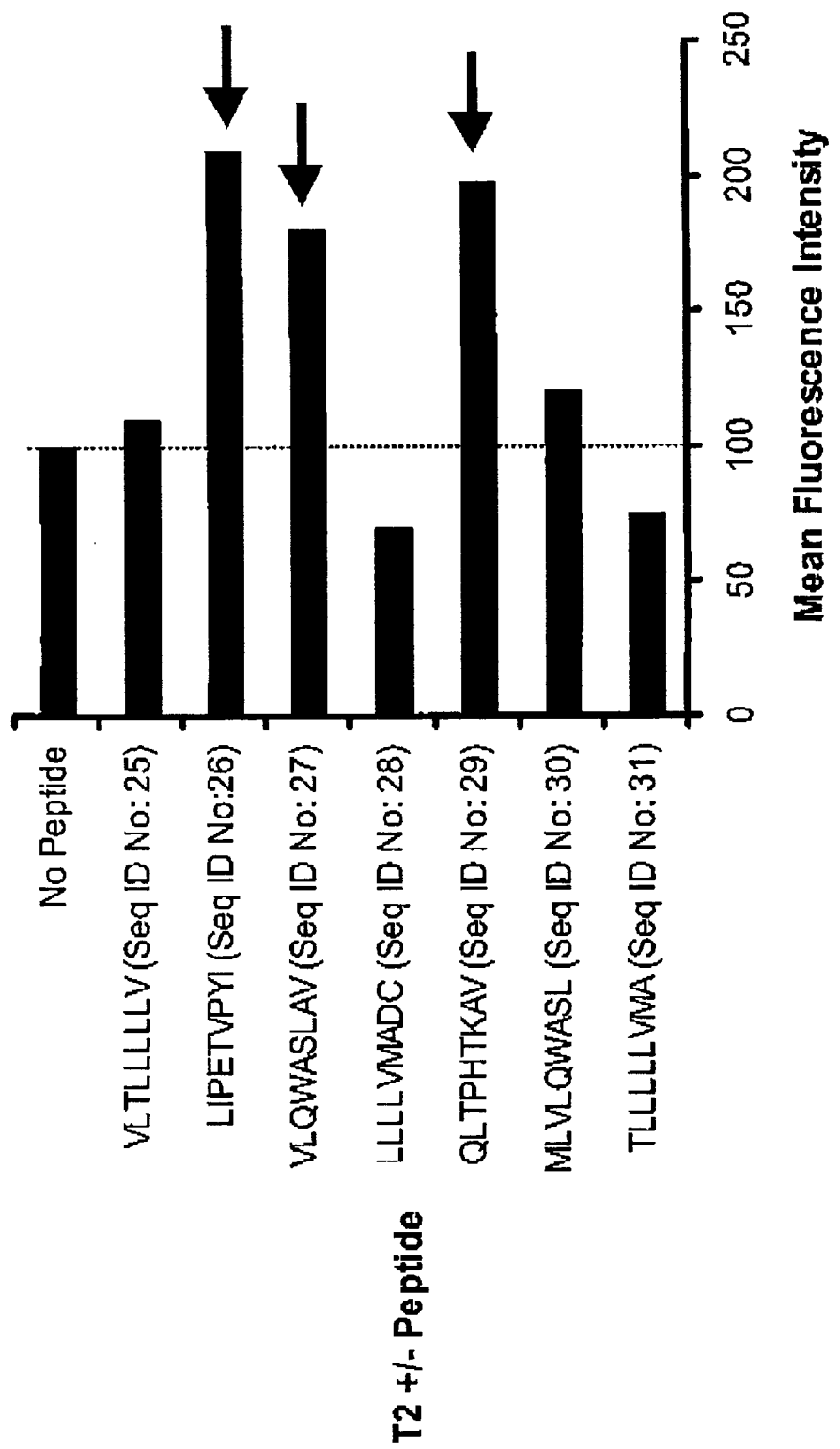

"To identify potential HLA A2 restricted epitopes within gp85 and gp350, the amino acid sequence was analyzed using the HLA Binding Predictions program of the Bioinformatics & Molecular Analysis Section of the Computational Biosciences and Engineering Lab, Center for Information Technology at the National Institutes for Health, 12 South Drive, MCS 5624 (Building 12A, Room 2033), Bethesda MD 20892, USA (18). A total of 20 peptides (13 from gp85 and 7 from gp350) with an estimated half-time disassociation score of >100 for gp85 and >50 for gp350 were selected (Table 3). These peptides were then tested for HLA A2 binding efficiency using HLA A2-positive T2 cells. Representative data from a series of experiments is presented in FIG. 8. This analysis showed that seven of these peptides significantly increased the expression of HLA A2 on T2 cells

TABLE 3

Identification of Potential HLA A2 Binding Peptides within gp85 and gp350*

| Ranking | Residue | Peptide Sequence | Score (Estimate half-time disassociation from HLA A2 allele) |
|---|---|---|---|
| gp85 peptides | | | |
| 1 | 177–185 | FLMGTYKRV (SEQ ID NO: 12) | 1775.663 |
| 2 | 317–325 | WLAKSFFEL (SEQ ID NO: 13) | 1082.903 |
| 3 | 672–680 | GLYEERAHV (SEQ ID NO: 14) | 912.522 |
| 4 | 685–693 | ILYFIAFAL (SEQ ID NO: 15) | 674.026 |
| 5 | 2–10 | QLLCVFCLV (SEQ ID NO: 16) | 488.951 |
| 6 | 225–233 | SLVIVTTFV (SEQ ID NO: 17) | 382.536 |
| 7 | 681–689 | VLAIILYFI (SEQ ID NO: 18) | 224.537 |
| 8 | 684–692 | IILYFIAFA (SEQ ID NO: 19) | 196.407 |
| 9 | 542–550 | LMIIPLINV (SEQ ID NO: 20) | 181.738 |
| 10 | 1–9 | MQLLCVFCL (SEQ ID NO: 21) | 181.738 |
| 11 | 7–15 | FCLVLLWEV (SEQ ID NO: 22) | 133.298 |
| 12 | 658–666 | YLLLTTNGT (SEQ ID NO: 23) | 126.883 |
| 13 | 420–428 | TLFIGSHVV (SEQ ID NO: 24) | 105.510 |
| gp350 peptides | | | |
| 1 | 871–879 | VLTLLLLV (SEQ ID NO: 25) | 271.948 |
| 2 | 152–160 | LIPETVPYI (SEQ ID NO: 26) | 126.481 |
| 3 | 863–871 | VLQWASLAV (SEQ ID NO: 27) | 118.238 |
| 4 | 875–883 | LLLLVMADC (SEQ ID NO: 28) | 71.872 |
| 5 | 67–75 | QLTPHTKAV (SEQ ID NO: 29) | 69.552 |
| 6 | 861–869 | MLVLQWASL (SEQ ID NO: 30) | 61.737 |
| 7 | 873–881 | TLLLLVMA (SEQ ID NO: 31) | 42.278 |

*To identify the potential HLA A2 binding peptides within gp85 and gp350, the HLA Binding Predictions program of the Bioinformatics & Molecular Analysis Section of the Computational Bioscience and Engineering Lab, Center for Information Technology at the National Institutes for Health, 12 South Drive, MCS 5624 (Building 12A, Room 2033), Bethesda MD 20892, USA, was employed as described elsewhere (ref 18). This program can be directly accessed through the world-wide web.

suggesting that these peptides might be potential HLA A2-restricted epitopes.

Recognition of the gp85 and gp350 Peptide Epitopes by IM Effectors Ex Vivo

Figure 9A:
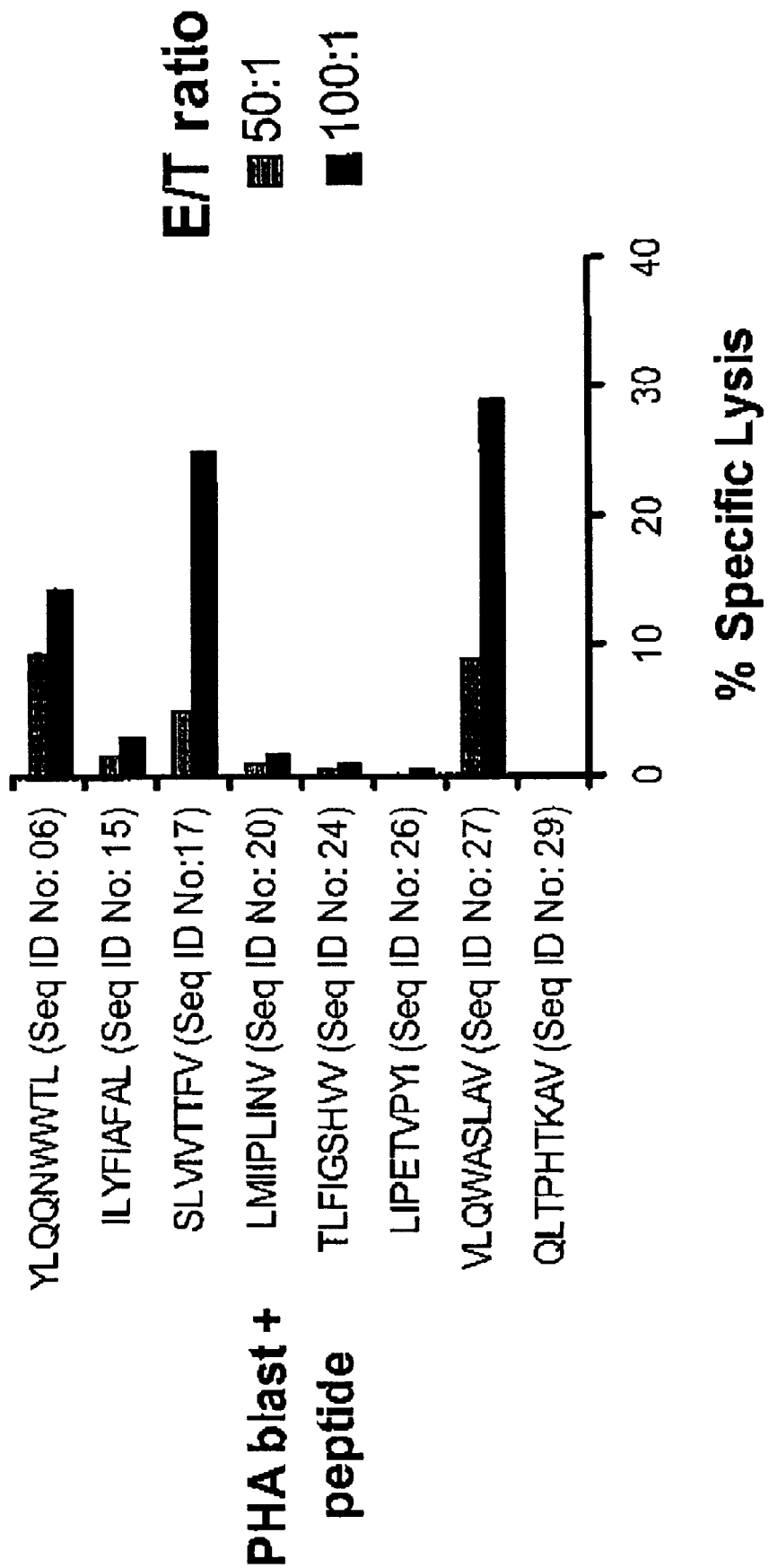
FIG. 9:gp85 and gp350-specific ex vivo cytotoxic T cell activity in peripheral blood lymphocytes from IM donors. Panel A, B & C shows ex vivo CTL lysis of peptide-sensitized (1 µg/ml) PHA blasts at two different effector-:target (E/T) ratios. Data from IM patient SB, LP and MG are presented in panel A, B and C respectively. Panel D shows ex vivo CTL lysis by peripheral blood lymphocytes from patient LP of target cells infected with recombinant vaccinia encoding either gp85 (Vacc.gp85) or gp350 (yacc.350) by. Vacc.TK- and Vacc.EBNA2 were used as control in the assay.
Figure 9B:
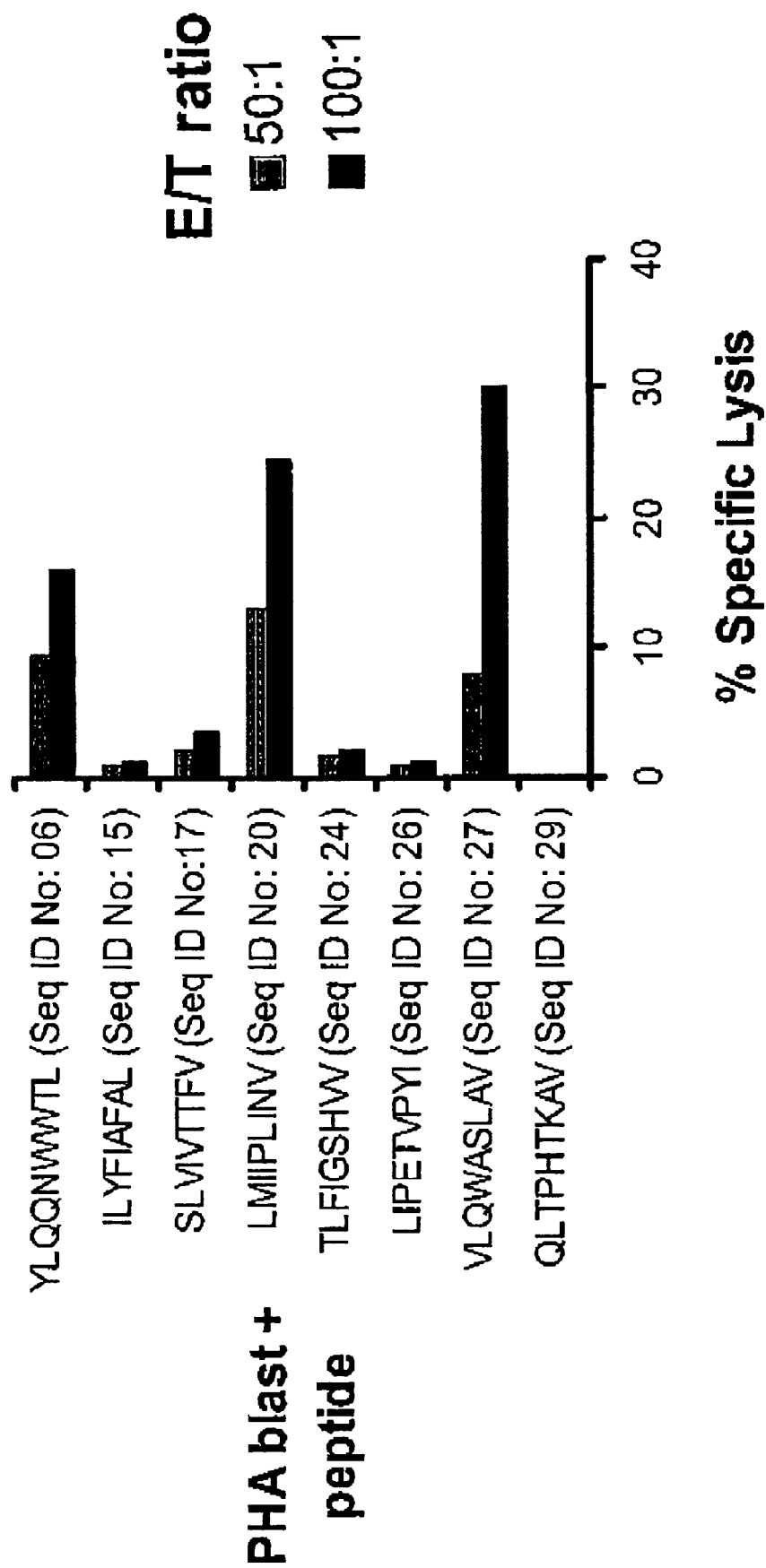
Figure 9C:
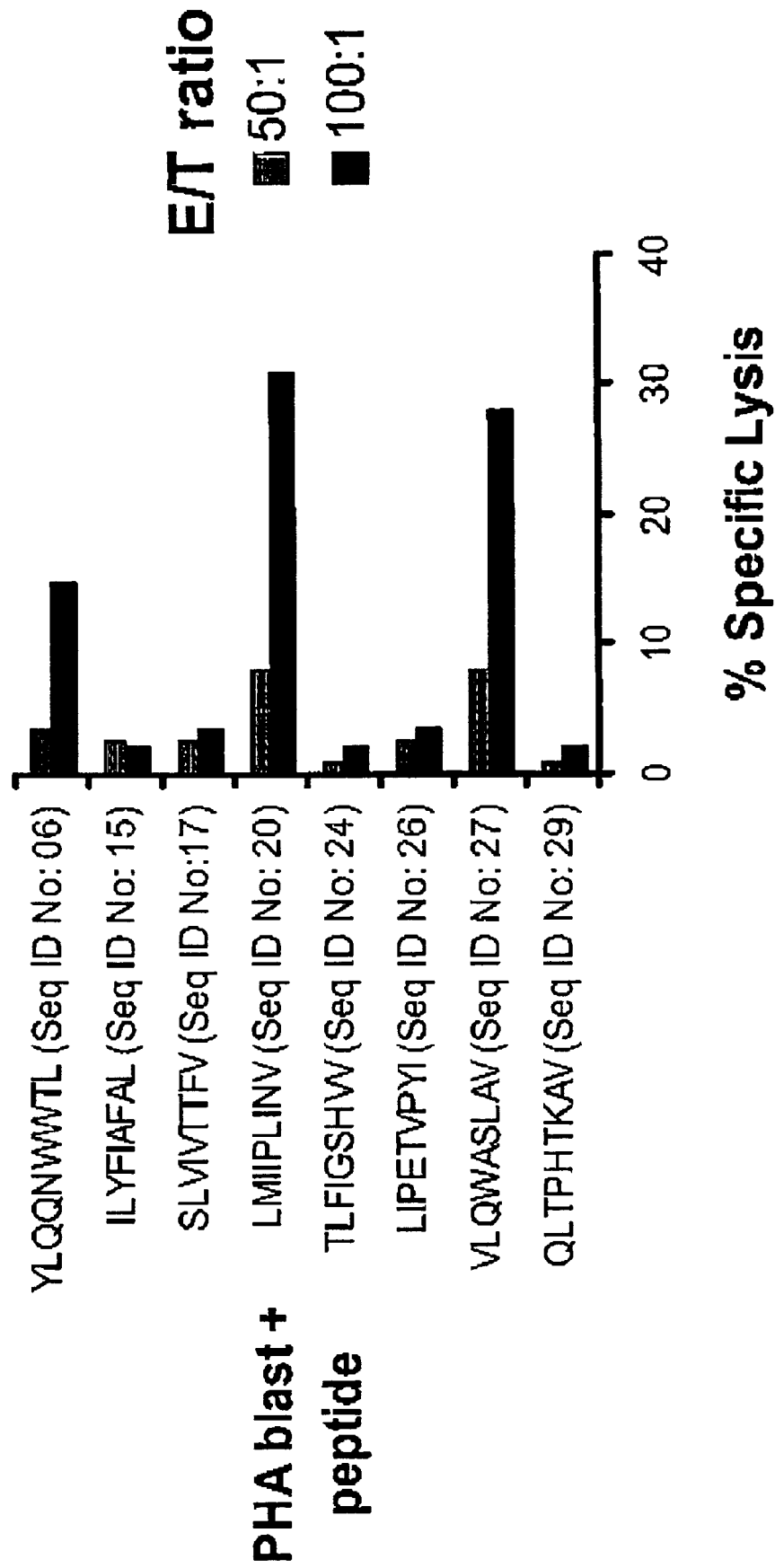
Figure 9D:
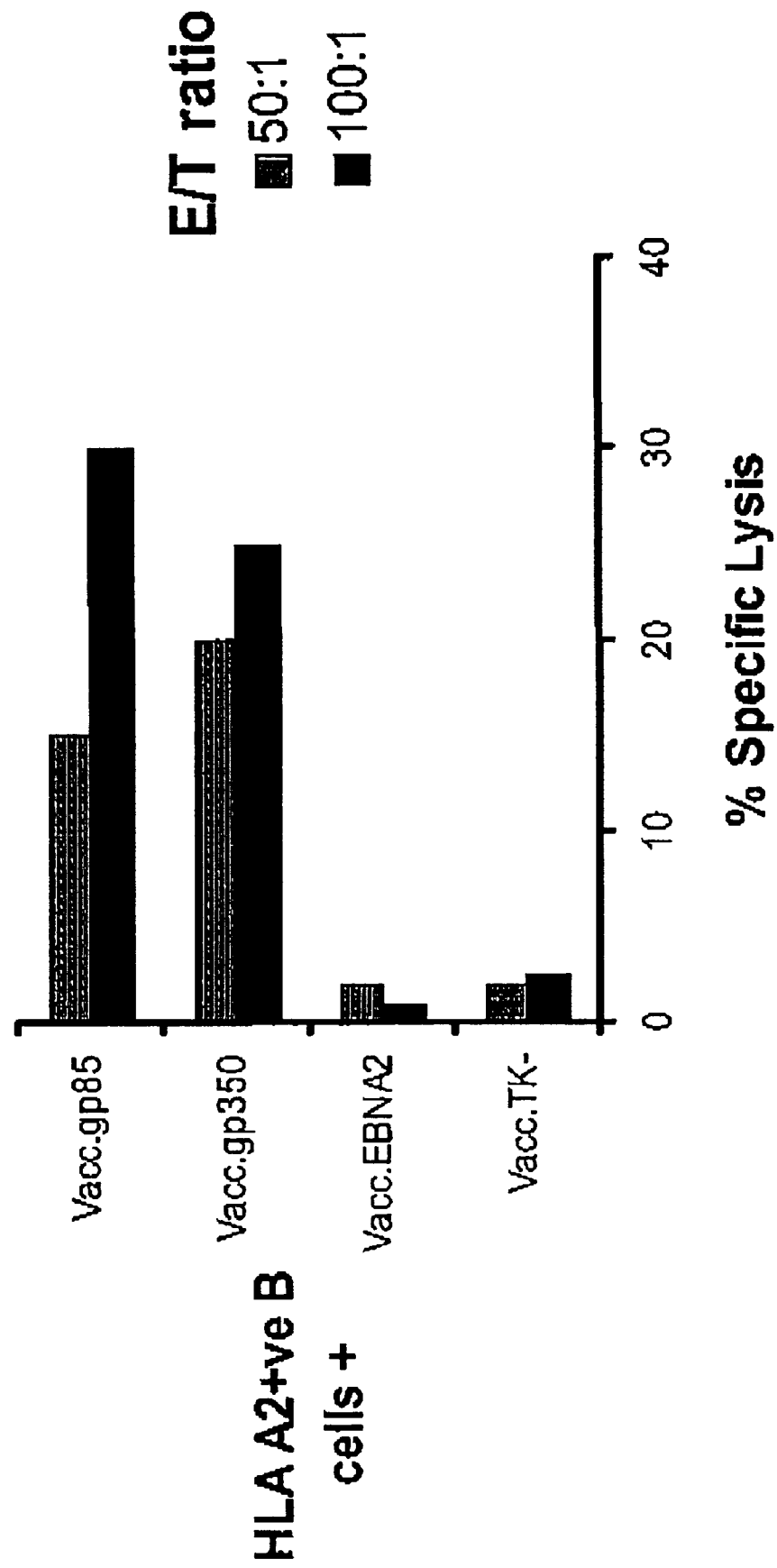

The seven HIA A2-binding peptides, which included four peptides from gp85 and three peptides from gp350 were next tested for CTL recogniton by effectors from IM patients. In addition, we also included an HLA A2-restricted CTL epitope from EBV latent mambrane protein (LMP1) as a positive control (38). PBMCs from three HIA A2-positive IM patients, SB, LP and MG were resuspended in IL2-supplemented growth medium and used as effectors in a standard 5lCr-release assay against HLA-matched PHA blasts sensitized with the gp85, gp350 or LMP1 peptides. Representative data from two different experiments is shown in FIGS. 9(A–C). Effectors from all three IM patients showed clear recognition of the reference LMP1 peptide (YLQQNWWTL (SEQ ID NO:6)) consistent with our earlier finding that this peptide is recognized by EBV-specific CTLs. More importantly, these IM patients also showed strong recognition of target cells sensitized with selected gp85 or gp350 peptides. Interestingly, each of these individuals showed a distinct pattern of reactivity against these peptides. IM patient SB showed strong reactivity against peptides SLV (SEQ ID NO:17) (gp85) and VLQWASLAV (SEQ ID NO:27) (gp350) (FIG. 9A), while the LP and MG effectors recognised target cells preloaded with peptides LMIIPLINV (SEQ ID NO:20) (gp85) and VLQWASLAV (SEQ ID NO:27) (gp350) (FIGS. 9(B–C)). Furthermore, ex vivo effectors from patient LP also recognised target cells infected with Vacc.gp350 and Vacc.gp85 (FIG. 9D).

In Vitro Expansion of gp85 and gp350 Peptide Epitope Reactive CTLs

Figure 10:
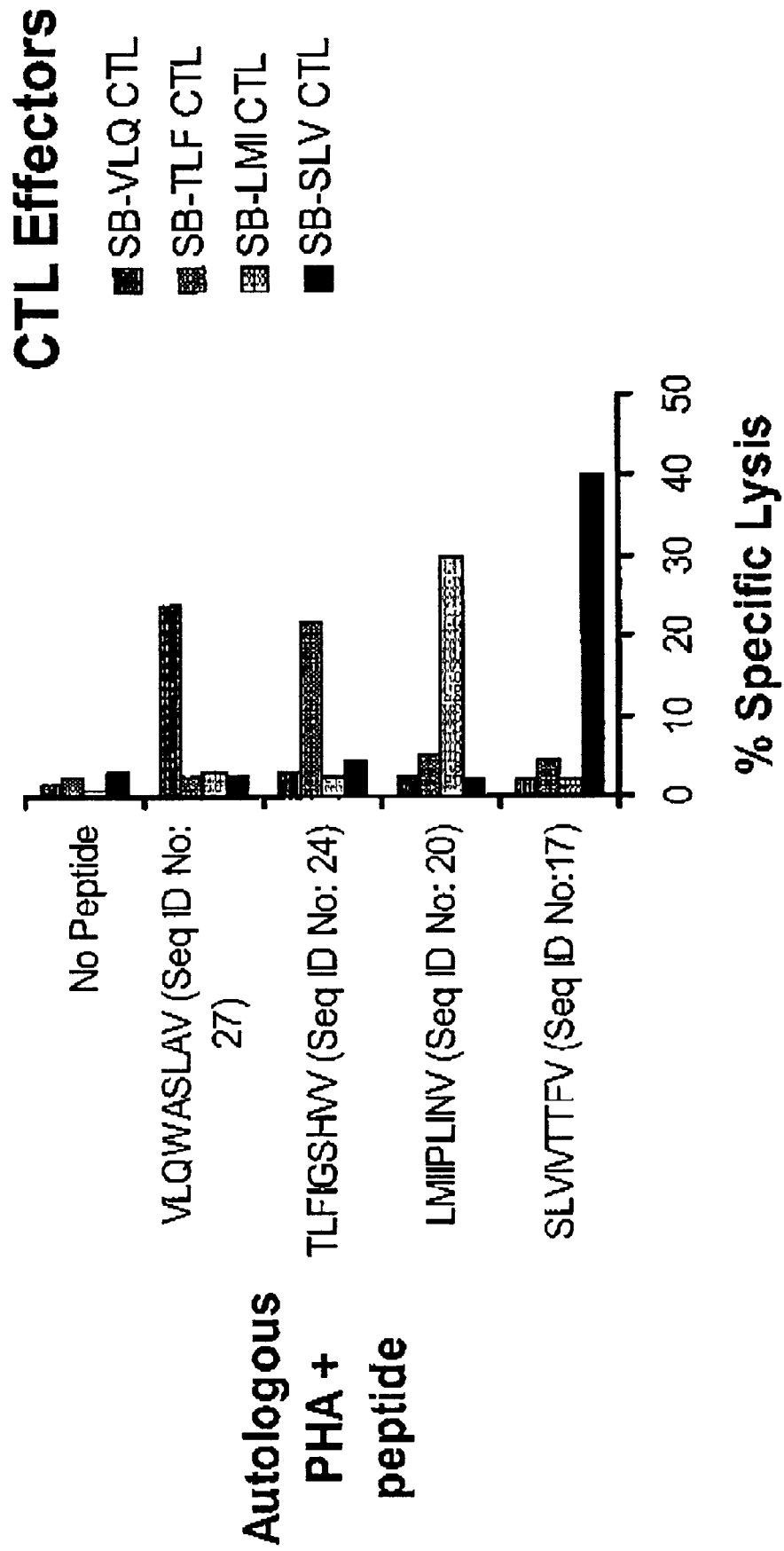
FIG. 10:Recognition of gp85 and gp350 peptides by polyclonal CTLs from an HLA A2-positive IM recovered (36 months post IM) individual. PBNIC were co-cultivated for seven days with irradiated T2 cells sensitized withsynthetic peptides (indicated on the Y-axis). On day 18, these cells were used as polyclonal effectors in a standard 5lCr-release assay against peptide-sensitized (1Tg/ml) autologous PHA blasts. An effector:target ratio of 20:1 was used in the assay. Individual peptide stimulated CTL effectors used in this experiments are indicated in the figure. Data from one representative experiment out of three is shown. Results are expressed as percent specific lysis.

The data presented above clearly demonstrate that gp85 and gp350 include CTL determinants which can bind HIA A2 molecules and are efficiently recognised by ex vivo effectors from IM patients. To determine whether gp85- or gp350-reactive CTLs can be detected following recovery from IM, PBMCs from the two donors SB and LP were collected at 24–36 months post IM respectively and were stimulated with T2 cells presensitized with each of the gp85 and gp350 peptides which showed strong HIA A2 binding. On day 18, these CTL effector were tested against peptide-sensitized autologous PHA blasts. Representative data from polyclonal CTLs from donor SB are presented in FIG. 10. CTL effectors from donor SB not only showed strong reactivity against peptides SLVIVTTFV (SEQ ID NO:17) and VLQWASLAV (SEQ ID NO:27) but also recognized two other peptides from gp85 (LMIIPLINV (SEQ ID NO:20) and TLFIGSHVV (SEQ ID NO:24)). Donor LP also showed a similar pattern of CTL lysis. Thus peptide TLFIGSHVV (SEQ ID NO:24) was a target for EBV-specific CTL recogntion in the memory response of these A2-positive individuals, but this response was not detectable with ex vivo effectors during acute infection. Another important point which needs to be highlighted here is that our attempts to activate gp85- or gp350-specific CTLs with autologus LCLs as stimulators were unsuccessful. This result is not surprising since it is well established that in latently infected B cells, gp350 or gp85 antigens are poorly expressed. The LCL-stimulated polyclonal T cell lines from these donors strongly reactive against latent antigens (data not shown). This obseravtion is consistent with our earlier studies which showed that CTL responses in healthy virus carriers is often dominated by reactivity to latent antigens (6). Another explanation for an inability to detect gp350- or gp85-specific CTL reactivity following stimulation with the autologous LCLs is that these responses may constitute a minor component of the total virus specific CTL -response in healthy virus carriers. Indeed, limiting dilution analysis for CTL precursors specific for the 8p350 or gp85 peptide epitopes in post IM donors SB and LP showed precursor frequencies of >1/50,000, while precursor frequencies for CTLs that recognise CTL epitopes within the latent antigens were between 1/4,000–1/15,000 (data not shown).

Figure 11A:
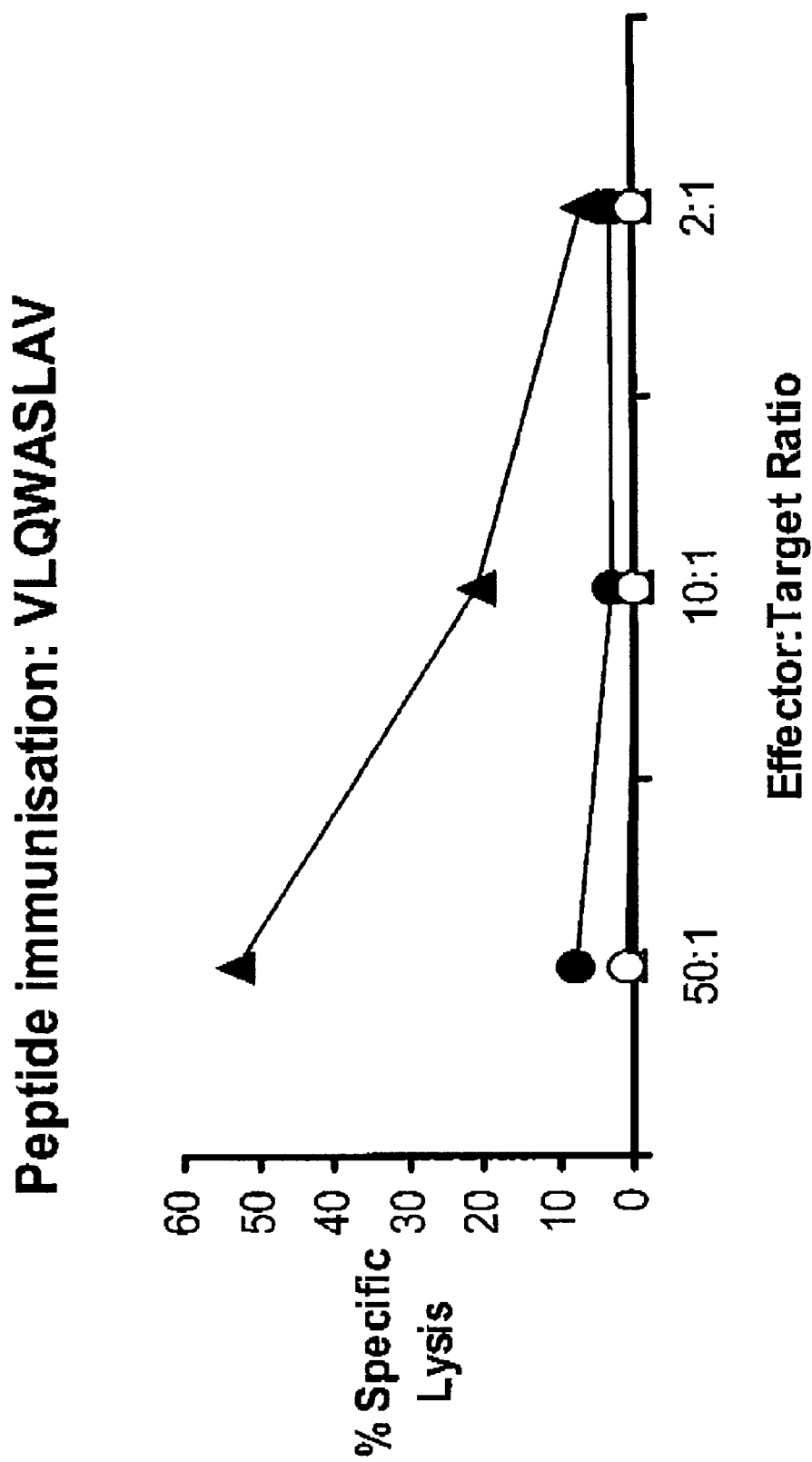
FIG. 11:Immunization of HLA A2/K$^b$ mice with gp85 and gp350 CTL epitopes induces strong CTL response. Animals were twice immunized (at a 14 day interval) subcutaneously with individual CTL epitope with Tetanus Toxoid as a source of help. Four weeks following peptide immunization, animals were assessed for gp350- and gp85-specific CTL response. Panel A, B & C shows CTL activity in splenocytes from two mice immtnized with VLQWASLAV (SEQ ID NO:27) (gp350), TLFIGSHVV (SEQ ID NO:24) (gp85) and SLVIVTTFV (SEQ ID NO:17) (gp85) respectively. CTL lysis of target cells sensitized with peptide epitopes are shown as filled symbols, while lysis of unsensitized target cells is shown as empty symbols. Panel D shows CTL activity in pooled inguinal lymphnodes from mice immunised with peptide VLQWASLAV (SEQ ID NO:27) (■, □). SLV (SEQ ID NO:17) (▼, Δ) and TLFIGSHVV (SEQ ID NO:24) (●, o). CTL activity was tested on day 6 using a standard 51Cr-release assay.
Figure 11B:
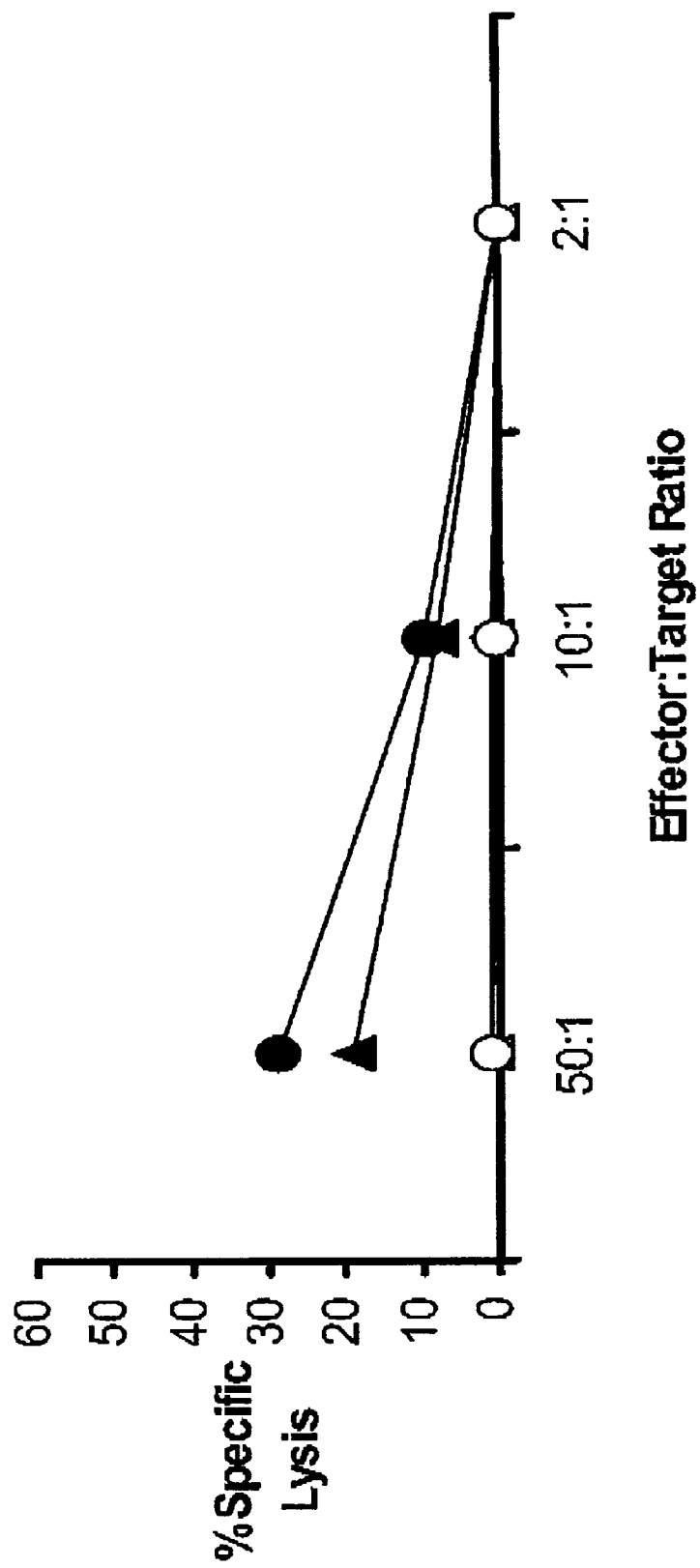
Figure 11C:
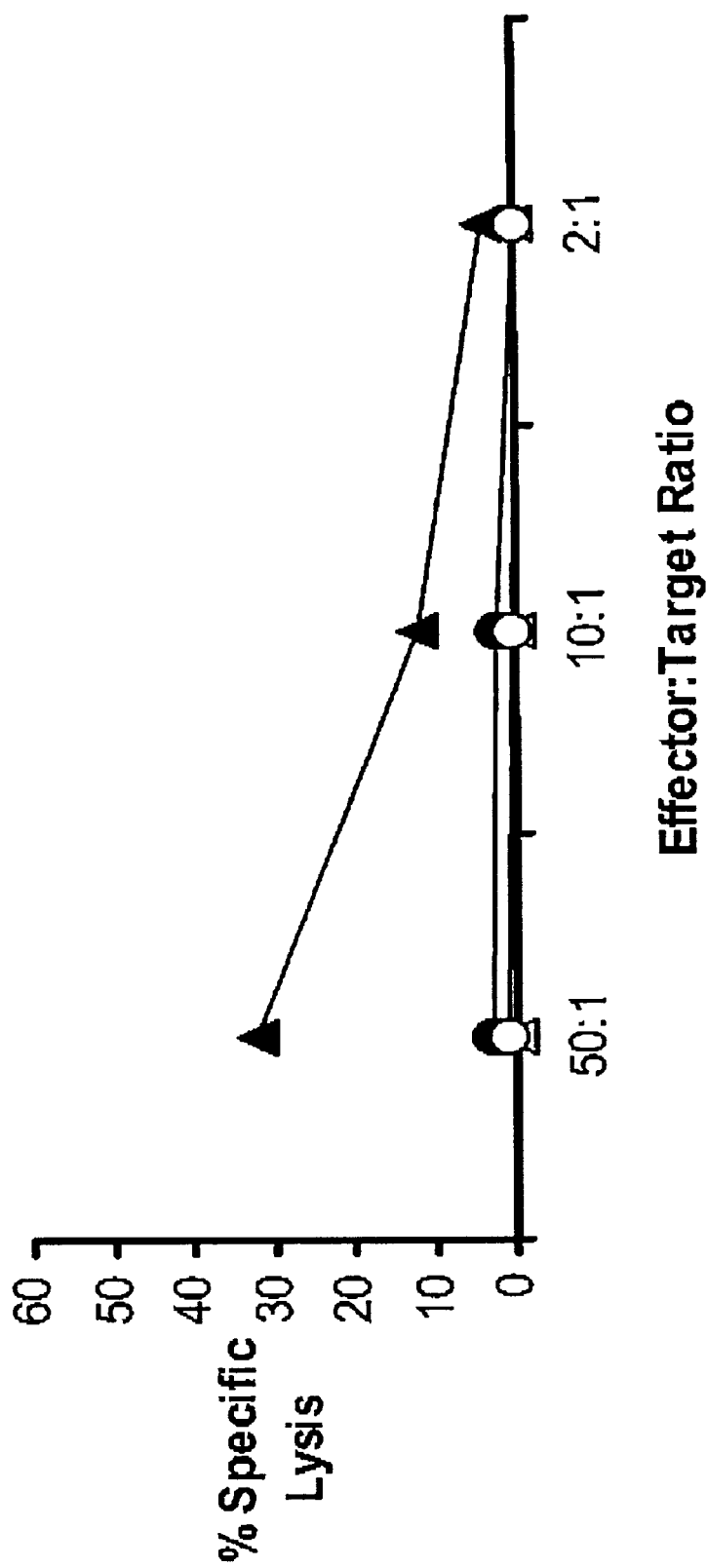
Figure 11D:
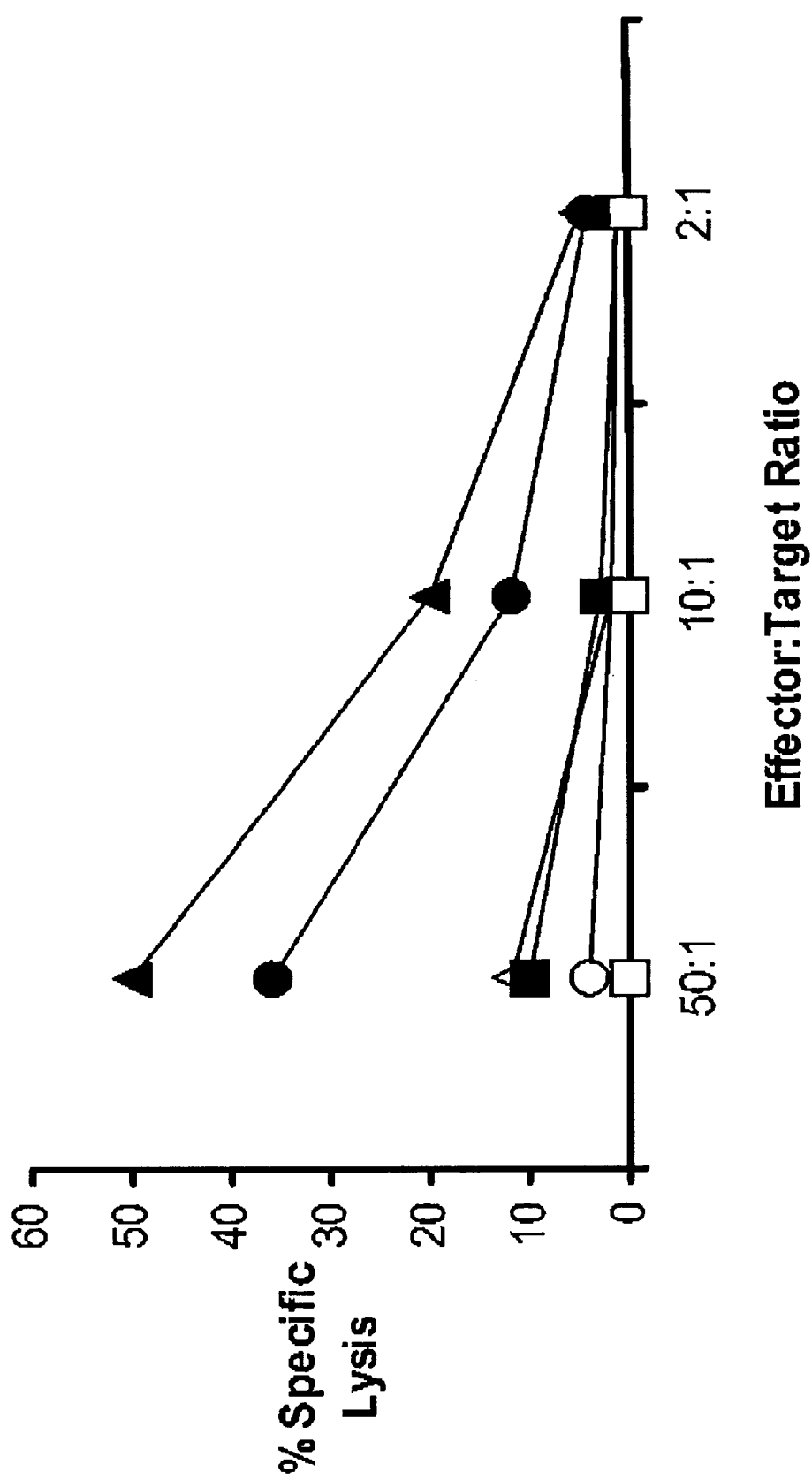

Immunization of HLA A2/Kb Mice with gp85 and gp350 Peptide Epitopes Induces Specific CTL Response Having established that gp85 and gp350 includes CTL epitopes, we extended our studies to explore the possibility of using these peptide epitopes to induce specific CTL response in vivo. HLA A2/Kb transgenic mice were used as an experimental model to address this issue. These mice express a chimeric class I molecule composed of the alpha 1 & 2 domains of the human A*0201 allele and the alpha 3 domain of the mouse H-2Kb class I molecules. These animals were immunized subcutaneously with gp350 or gp85 CTL epitopes emulsified in IFA together with Tetanus Toxoid as a source of help. The SLVIVTTFV (SEQ ID NO:17) and TLFIGSHVV (SEQ ID NO:24) peptides from gp85 and the VLQWASLAV (SEQ ID NO:27) peptide from gp350 were used for immunisation. Two weeks following immunization, specific CTL response was assessed in each mouse using splenocytes or pooled inguinal lymph node cells as effectors. Data presented in FIGS. 11(A–C) demonstrate that peptide epitopes from gp85 (SLVIVTTFV (SEQ ID NO:17) and TLFIGSHVV (SEQ ID NO:24)) and gp350 (VLQWASLAV (SEQ ID NO:27)) induced strong CTL response in splenocytes. Interestingly, CTLs activated from splenocytes with peptide TLFIGSHVV (SEQ ID NO:24) consistently showed strong lysis of targets, while splenocytes from SLVIVTTFV (SEQ ID NO:17) and VLQWASLAV (SEQ ID NO:27) immunized mice showed variable in vitro CTL lysis. A strong specific CTL activity was also noticed in pooled lymphocytes from inguinal lymph nodes (FIG. 11D).

Figure 12:
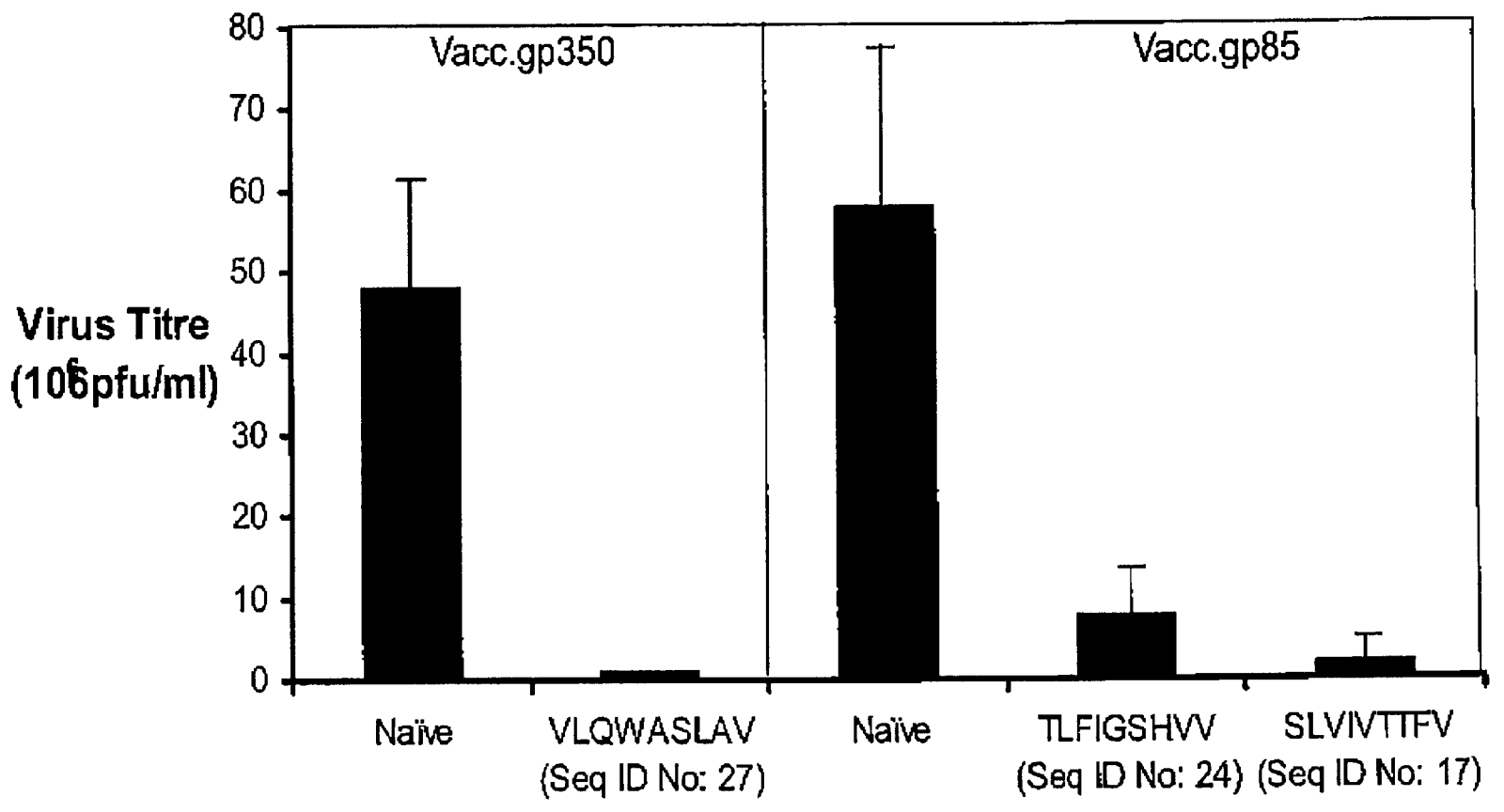

Prior Immunisation of HLA A2/Kb mice with gp85 or gp350 CTL Epitopes Affords Protection Against Recombinant Vaccinia Virus Challenge Four weeks after peptide immunization with gp85 or gp350 CTL epitopes, HLA A2/K b mice were challenged with $10^7$ pfu of recombinant vaccinia virus encoding either gp85 or gp350. After four days of challenge, these animals were sacrificed and vaccinia titres measured in both ovaries by plaque assay on confluent CV1 cells. Data from one such experiment is presented in FIG. 12. Animals immunised with gp85 and gp350 epitopes showed very low to undetectable virus in their ovaries, while in naive mice very high titres of vaccinia virus were detected. This protection correlated with strong induction of epitope-specific CTL responses detected in the splenocytes and lymph node cells collected four weeks after primary peptide vaccination in HLA A2/Kb transgenic mice.

Discussion

There is increasing interest in formulating an effective vaccine against EBV, designed to not only limit the outgrowth of latently infected B cells in healthy individuals but to also block the development of many EBV-associated malignancies such as Burkitt's lymphoma (BL). nasopharyngeal carcinoma (NPC) and Hodgkin's disease (HD). In western societies, the principle aim of such a vaccine would be to protect from IM. In this context. virus load (a large dose of orally transmitted virus and/or overexpansion of the virus-transformed B cell pool beyond a critical threshold) may be a critical determinant of disease risk (7). Therefore, a vaccine capable of either blocking primary EBV infection or significantly reducing the EBV load during primary infection may be adequate to avert clinical symptoms. A similar vaccine will also be able to reduce the immediate risk of lymphoproliferative disease in transplant patients receiving immunosuppressive therapy. On the other hand, EBV-associated malignancies such as BL, NPC, and HD arise in patients years after their primary infection, and protection from these longer-term consequences would require a vaccine that ideally confers sterile immunity and prevents the establishment of the carrier state.

EBV structural antigens, primarily gp350, have long been considered as the potential candidates for an EBV vaccine. The suggestion that gp350 is a likely vaccine candidate was based initially upon the observation that this glycoprotein is the principal target of the virus-neutralizing antibody response (41). A number of recombinant formulations of gp350, either presented as a subunit antigen or expressed from recombinant viral vectors, designed to induce high titre neutralizing antibodies, have shown significant protection against EBV-induced B cell lymphomas in cotton-top tamarins (31). However, development of neutralizing antibodies in vaccinated animals does not always shows limited correlation with protection from EBV infection, although recent results have suggested a role for gp350-specific CTLs in this protection (34). If the latter suggestion is correct, it is important to identify the potential CTL determinants within EBV structural proteins since it is now well established that immunization with whole viral proteins is unable to elicit an efficient CTL response. Moreover, a vaccine based on CTL epitopes provides an opportunity to include determinants not only from gp350 but also from other structural antigens, such as gp85. To address this issue we have used a novel protocol to successfully identify CTL epitopes within gp350 and gp85. In the first set of experiments we identified HIA A2 binding peptides within gp350 and gp85. Subsequent experiments were focussed on IM patients with the HLA A2 allele. Using ex vivo primary effectors, we observed strong reactivity to three different gp350 and gp85 peptides. Interestingly, individual IM patients showed distinct patterns of reactivity to each of these peptides. Strong reactivity against peptides SLVIVTTFV (SEQ ID NO:17) (gp85) and VLQWASLAV (SEQ ID NO:27) (gp350) was observed with ex vivo effectors from patient SB, while the LP and MG effectors recognized target cells preloaded with LMIIPLINV (SEQ ID NO:20) (gp85) and VLQWASLAV (SEQ ID NO:27) (gp350) peptides. More importantly, ex vivo effectors from patient LP also recognised target cells infected with Vacc.gp350 and Vacc.gp85. Interestingly, the level of ex vivo CTL lysis directed to epitopes from structural antigens was consistently higher than those seen in the same assays against HLA A2-restricted CTL epitopes from a latent antigen. These results are consistent with recent observations by Steven and colleagues (42) that ex vivo CTL reactivity to lytic antigens in IM patients is significantly higher compared to latent antigens.

In the next set of experiments, we explored the possibility of detecting structural antigen-specific CTL responses in individuals following resolution of IM symptoms. This follow up analysis was carried out 24–36 months post acute IM. Our initial attempts to isolate gp350- or gp85-specific CTLs from post IM donors by stimulating with the autologous LCL were unsuccessful. Subsequently we used peptide loaded T2 cells as stimulators to generate gp350- and gp85-specific CTLs. We have recently shown that this method can be successfully used to raise low frequency EBV-specific CTL precursors (38). Stimulation of PBMC from donors SB and LP raised strong CTL responses to the gp85 and gp350 CTL epitopes. Both donors SB and LP not only showed reactivity against peptides SLVIVTTFV (SEQ ID NO:17), LMIIPLINV (SEQ ID NO:20) and VLQWASLAV (SEQ ID NO:27) but also recognized another peptide from gp85, TLFIGSHVV (SEQ ID NO:24). It is interesting to note here that both donors showed no ex vivo CTL reactivity to TLFIGSHVV (SEQ ID NO:24) during acute IM. One of the important conclusions drawn from these analyses is that, following recovery from acute IM, there is a significant reduction in CTL precursors to the structural antigens, and the response becomes dominated by CTL reactive to the latent antigens. Indeed, limiting dilution analysis for CTL precursors specific for the gp350 or gp85 peptide epitopes in donors SB and LP post IM showed frequencies of >1/50,000, while precursor frequencies for CTL epitopes within latent antigens were between 1/4,000–1/15,000.

The detection of a strong ex vivo CTL response in IM patients to the structural antigens has important implications for any future vaccine design. As mentioned above, to date, the major emphasis of vaccine design based on EBV structural antigens has been directed towards generating a strong neutralizing antibody response. However, these neutralizing antibody response fail to correlate with protection against EBV-induced polyclonal lymphomas in cotton-top marmosets. Nevertheless, it is possible that this protection is mediated by structural antigen-specific CTL responses. To address this issue, we employed an experimental animal model system to determine whether gp350 or gp85 Cm epitope immunized transgenic mice, expressing the human HLA A2 antigen, are capable of (a) generating structural antigen-specific CTL responses and (b) reducing infection with a recombinant vaccinia virus infection expressing the gp350 or gp85 antigen. These mice not only showed induction of a strong CTL response following immunization but also acquired strong resistance to virus infection. It is important to mention here that although this experiment does not allow any firm conclusions on the efficacy of a gp350 and/or gp85 CTL epitope based vaccine in humans, it does clearly show that CTL epitopes from the EBV structural antigens can be used as immunogens to induce an efficient CTL response in vivo. Moreover, this approach also overcomes limitations of whole gp350 or gp85 proteins which might be inefficient at eliciting CTL responses in humans. Obviously one of the possible obstacles of any epitope-based approach to vaccination in humans is HLA polymorphism because epitope choice is allele-specific. However, this obstacle might be overcome using appropriate mixtures of synthetic peptide epitope or by constructing vectors to express polypeptides in which the relevant epitope sequences are linearly joined together. Indeed, earlier studies from our laboratory have shown that if such an EBV polyepitope sequence is expressed within cells from a recombinant vaccinia vector, all of the constituent epitopes are efficiently presented for CTL recognition (43), indicating the potential of this approach as a vaccine strategy. More recently, work in a murine model has also shown that each of several CTL epitopes combined in a polyepitope construct was capable of eliciting a CTL response in vivo and could protect the animals from subsequent challenge (44). In the long term, it may be possible to combine CTL epitopes from the EBV structural antigens, with latent antigen epitopes generating a chimeric protein that fuses the important immunogenic determinants from the two different types of antigens to design an effective vaccine.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Bibliography

1. Burrows, J. M., S. R. Burrows, L. M. Poulsen, T. B. Sculley, D. J. Moss, and R. Khanna. 1996. Unusually high freqency of Epstein-Barr virus genetic variants in Papua New Guinea that can escape cytotoxic T-cell recognition: implications for virus evolution. J. Virol. 70:2490–2496.
2. Burrows, S. R., S. J. Rodda, A. Suhrbier, H. M. Geysen, and D. J. Moss. 1992. The specificity of recognition of a cytotoxic T lymphocyte epitope. Eur. J. Immunol. 22:191–195.
3. Fahraeus, R., L. Rymo, J. S. Rhim, and G. Klein. 1990. Morphological transformation of human keratinocytes expressing the LMP gene of Epstein-Balr virus Morphological transformation of human keratinocytes expressing the LMP gene of Epstein-Barr virus. Nature 345:447–449.
4. Fazekas de St Groth, S. 1982. The evaluation of limiting dilution assays. J. Immunol. Methods 49:R11–23.
5. Henderson, S., M. Rowe, C. Gregory, D. Croom-Carter, F. Wang, R. Longnecker, E. Kieff, and A. B. Rickinson. 1991. Induction of bcl-2 expression by Epstein-Barr virus latent membrane protein 1 protects infected B cells from programmed cell death. Cell 65:1107–1115.
6. Khanna, R., S. R. Burrows, M. G. Kurilla, C. A. Jacob, I. S. Misko, T. B. Sculley, E. Kieff, and D. J. Mloss. 1992. Localization of Epstein-Barr virus cytotoxic T-cell epitopes using recombinant vaccinia:implications for vaccine development. J. Exp. Med. 176:169–176.
7. Khanna, R., S. R. Burrows, and D. J. Moss. 1995. Immune regulation in Epstein-Barr virus-associated diseases. Microbiol. Rev. 59:387–405.
8. Khanna. R., S. R. Burrows, S. L. Silins, D. J. Moss, L. M. Poulsen, and J. M. Burrows. 1996. Cytotoxic T-lymphocyte clones specific for an immunodominant epitope display discerning antagonistic response to naturally occurring Epstein- Barr virus variants. J. Virol. 70:7306–7311.
9. Khanna, R., S. R. Burrows, A. Suhrbier, C. A. Jacob, H. Griffin, I. S. Misko, T. B. Sculley, M. Rowe, A. B. Rickinson, and D. J. Moss. 1993. EBV peptide epitope sensitization restores human cytotoxic T cell recognition of Burkitt's lymphoma cells. Evidence for a critical role for ICAM-2. J. Immunol. 150:5154–5162.
10. Khanna, R., S. R. Burrows, S. A. Thomson. D. J. Moss, P. Cresswell, P. Poulsen, and L. Cooper. 1997. Class I processing defective Burkitt's lymphoma cells are recognised efficiently by CD4+EBV-specific CmL. J Immunol 157:3619–3625.
11. Khanna, R., C. A. Jacob, S. R. Burrows, M. G. Kurilla. E. Kieff, I. S. Misko. and D. J. Moss. 1991. Expression of Epstein-Barr virus nuclear antigens in anti-IgM-stimulated B cells following recombinant vaccinia infection and their recognition by human cytotoxic T-cells. Immunology 74:504–510.
12. Khanna, R., C. A. Jacob, S. R. Burrows, and D. J. Moss. 1993. Presentation of endogenous viral peptide epitopes by anti-CD40 stimulated human B cells following recombinant vaccinia infection. J. Immunol. Methods 164:41–49.
13. Krausa, P., M. Brywka,3rd, D. Savage. K. M. Hui. NWI. Bunce, J. L. Ngai, D. L. Teo. Y. W. Ong, D. Barouch, and C. E. Allsop. 1995. Genetic polymorphism within HLA-A*02:significant allelic variation revealed in different populations. Tissue Antigens. 45:223–231.
14. Lee, S. P., L. E. Wallace, M. Mackett, J. R. Arrand, P. F. Searle. NI. Rowe. and A. B. Rickinson. 1993. MHC class II-restricted presentation of endogenously synthesized antigen:Epstein-Barr virus transformed B cell lines can present the viral glycoprotein gp340 by two distinct pathways. Int. Immunol. 5:451–460.
15. Nieggetto, F., P. Broussel. J. Selves, G. Delsol. and B. Mariame. 1997. Reed-Sternberg cells and "bystander" lymphocytes in lymph nodes affected by Hodgkin's disease are infected with different strains of Epstein-Barr virus J. Virol. 71:2547–2549.
16. Moss, D. J., I. S. Misko, S. R. Burrows, K. Burman, R. McCarthy, and T. B. Sculley. 1988. Cytotoxic T-cell clones discriminate between A- and B-type Epstein-Barr virus transformants. Nature 331:719–721.

17. Murray, R. J., M. G. Kurilla, J. M. Brooks, W. A. Thomas, M. Rowe, E. Kieff, and A. B. Rickinson. 1992. Identification of target antigens for the human cytotoxic T-cell response to Epstein-Barr virus (EBV):implications for the immune control of EBV-positive malignancies. J. Exp. Med. 176:157–168.
18. Parker, K. C., M. A. Bednarek, and J. E. Coligan. 1994. Scheme for ranking potential HLA-A2 binding peptides based on independent binding of individual peptide sidechains. J. Immunol. 152:163–175.
19. Rickinson, A. B., S. Finerty. and M. A. Epstein. 1977. Comparative studies on adult donor lymphocytes infected by EB virus in vivo or in vitro: origin of transformed cells arising in co-cultures with foetal lymphocytes. Int. J. Cancer 19:775–782.
20. Rooney, C. M., M. Rowe, L. E. Wallace, and A. B. Rickinson. 1985. Epstein-Barr virus-positive Burkitt's lymphoma cells not recognized by virus-specific T-cell surveillance. Nature 317:629–631.
21. Rowe, M., D. T. Rowe, C. D. Gregory, L. S. Young, P. J. Farrell,. H. Rupani, and A. B. Rickinson. 1987. Differences in B cell growth phenotype reflect novel patterns of Epstein-Barr virus latent gene expression in Burkitt's lymphoma cells. EMBO J. 6:2743–2751.
22. Salter. R. D. and P. Cresswell. 1986. Impaired assembly and transport of HLA-A and -B antigens in a mutant T×B cell hybrid. EMBO J. 5:943–949.
23. Sample, J. and E. Kieff. 1990. Transcription of the Epstein-Barr virus genome during latency in growth-transformed lyniphocytes. J. Virol. 64:1667–1674.
24. Sculley, T. B., D. G. Sculley, J. H. Pope, G. W. Bornkamm, G. M. Lenoir, and A. B. Rickinson. 1988. Epstein-Barr virus nuclear antigens 1 and 2 in Burkitt lymphoma cell lines containing either 'A' - or 'B'-type virus. Intervirology 29:77–85.
25. Wang, D., D. Liebowitz, and E. Kieff. 1985. An EBV membrane protein expressed in immortalized lymphocytes transforms established rodent cells. Cell 43:831–840.
26. Wang, D., D. Liebowitz, and E. Kieff. 1988. The truncated form of the Epstein-Barr virus latent-infection membrane protein expressed in virus replication does not transform rodent fibroblasts. J. Virol. 62:2337–2346.
27. Wang, J. H Y. W. Yan. T. P. Garrett, J. H. Liu, D. W. Rodgers, R. L. Garlick, G. E. Tarr, Y. Husain, E. L. Reinherz, and S. C. Harrison. 1990. Atomic structure of a fragment of human CD4 containing two immunoglobulin-like domains. Nature 348:411–418.
28. Young, L. S., C. W. Dawson, D. Clark, H. Rupani, P. Bussoni, T. Tursz, A. Johnson. and A. B. Rickinson. 1988. Epstein-Barr virus gene expression in nasophaiyngeal carcinoma. J. Gen. Virol. 69:1051–1065.
29. Fahraeus, R., H. L. Fu, I. Ernberg, J. Finke, M. Rowe, G. Klein. K. Falk, E. Nilsson, M. Yadav and P. Busson. 1988. Expression of Epstein-Barr virus-encoded proteins in nasopharyngeal carcinoma. Int. J. Cancer 42:329–338.
30. Rooney, C. M., C. A. Smith, C. Y.Ng, S. Loftin, C. Li, R. A. Krahce, M. K. Brenner, H. E. Heslop. 1995. Use of gene-modified virus-specific T lymphocytes to control Epstein-Barr-virus-related lymphoproliferation. Lancet 345:9–13.
31. Nlorgani A. J. 1992. Epstein-Barr virus vaccines. Vaccine 10:563.
32. Morgan, A. J., S. Finerty, K. Lovgren, F. T. Scullion, and B. Morein. 1988. Prevention of Epstein-Barr (EB) virus-induced lymphonia in cottontop tamarins by vaccination with the EB virus envelope glycoprotein gp340 incorporated into immune-stimulating complexes. J. Gen. Virol. 69:2093.
33. Morgan, A. J., M. Mackett, S. Finerty, J. R. Arrand, F. T. Scullion, and M. A. Epstein. 1988. Recombinant vaccinia virus expressing Epstein-Barr virus glycoprotein gp340 protects cottontop tamarins against EB virus-induced malignant lymphomas. J. &led. Virol. 25:189.
34. Wilson, A. D., M. Shooshstari, S. Finerty, P. Watkins, and A. J. Morgan. 1996. Virus-specific cytotoxic T cell responses are associated with immunity of the cottontop tamarin to Epstein-Barr virus (EBV). Clin. Exp. Immunol. 103:199.
35. Yao, Q. Y., M. Rowe, A. J. Morgan, C. K. Sam, U. Prasad, H. Dang, Y. Zeng, and A. B. Rickinson. 1991. Salivary and serum IgA antibodies to the Epstein-Barr virus glycoprotein gp340:incidence and potential for virus neutralization. Int. J. Cancer 48:45.
36. Burrows, S. R., I. S. Misko, T. B. Sculley, C. Schmidt, and D. J. Moss. 1990. An Epstein-Barr virus-specific cytotoxic T-cell epitope present on A-and b-type transformants. J. Virol. 64:3974.
37. Khanna, R. 1998. Tumour surveillance:missing peptides and MHC molecules. Immunol. Cell Biol. 76:20.
38. White, C. A., S. M. Cross, M. G. Kurilla, B. M. Kerr, C. Schmidt, I. S. Misko, R. Khanna, and D. J. Moss. 1996. Recruitment during infectious mononucleosis of CD3+ CD4+CD8+virus- specific cytotoxic T cells which recognise Epstein-Barr virus lytic antigen BHRF1. Virology 219:489.
39. Vitiello, A., D. Marchesini, J. Furze, L. A. Sherman. and R. W Chesnut. 1991. Analysis of the HLA-restricted influenza-specific cytotoxic T lymphocyte response in transgenic mice carrying a chimeric human-mouse class I major histocompatibility complex. J. Exp. Med. 173:1007.
40. Vitiello. A., A. Sette, L. Yuan. P. Farness, S. Southwood, J. Sidney. R. W. Chesnut, H. M. Grey, and B. Livingston. 1997. Comparison of cytotoxic T lymphocyte responses induced by peptide or DNA immunization:
implications on immunogenicity and immunodominance. Eur. J. Immunol. 27:671.
41. Thorley-Lawson, D. A. 1980. The suppression of Epstein-Barr virus infection in vitro occurs after infection but before transformation of the cell. J. Immunol. 124:745.
42. Steven, N. M., N. E. Annels, A. Kumar, A. M. Leese, M. G. Kurilla, and A. B. Rickinson. 1997. Immediate early and early lytic cycle proteins are frequent targets of the Epstein-Barr virus-induced cytotoxic T cell response. J. Exp. Med. 185:1605.
43. Thomson, S. A., R. Khanna, J. Gardner, S. R. Burrows, B. Coupar, D. J. Moss, and A. Suhrbier. 1995. Minimal epitopes expressed in a recombinant polyepitope protein are processed and presented to CD8+ cytotoxic T cells: implications for vaccine design. Proc. Natl. Acad. Sci. U. S A. 92:5845.
44. Thomson, S., S. Elliott, M. Sherritt, K. W. Sproat, B. E. Coupar, A. A. Scalzo, C. A. Forbes, A. Ladhams, X. Y. Mo, R. Tripp, P. C. Doherty, D. J. Moss, and A. Suhrbier. 1996. Recombinant polyepitope vaccines for the delivery of multiple CD8+cytotoxic T cell epitopes. J Immunol 157:822–826.
45. Crawford et al (1980). Lancet 1:1355–1356.
46. Crawford, D. H. and Thomas, J. A. (1993). Epstein-Barr virus-associated lymphoma in The Epstein-Barr virus and Associated Diseases eds:T Turz, J. S. Pagano, G. de The, G.Lenoir, G. R. Pearson INSERM/John Libbey Eurotext vol 225, pp397–404
47. Randhawa et al (1990) Am J Surg Pathol 14:538–547.
48. Rickinson et al (1997). Annual Review of Immunology. 15:405–431.6
49. Thomas et al (1991). Adv. Cancer Res. 57:329–380.

What is claimed is:

1. An isolated peptide consisting of a cytotoxic T-cell epitope having an amino acid sequence selected from the group consisting of YLLEMLWRL (SEQ ID NO:1), YFLEILWGL (SEQ ID NO:32), YLLEILWRL (SEQ ID NO:33), YLQQNWWTL (SEQ ID NO:6), LLLALLFWL (SEQ ID NO:2), LLVDLLWLL (SEQ ID NO:3), LLLIAL-WNL (SEQ ID NO:4), WLLLFLAIL (SEQ ID NO:5), TLLVDLLWL (SEQ ID NO:7), LLWLLLFLA (SEQ NO:8), ILLIIALYL (SEQ ID NO:9), VLFIFGCLL (SEQ ID NO:10), RLGATIWQL (SEQ ID NO:11), ILYFIAFAL (SEQ ID NO:15), SLVIVTTFV (SEQ ID NO:17), LMII-PLINV (SEQ ED NO:20), TLFIGSHVV (SEQ ID NO:24), LIPETVPYI (SEQ ID NO:26), VLQWASLAV (SEQ ID. NO:27) and QLTPHTKAV (SEQ ID NO:29).

2. The isolated peptide of claim 1 wherein the cytotoxic T-cell epitope has an amino acid sequence selected from the group consisting of YLLEMLWRL (SEQ ID NO:1), YLLEILWRL (SEQ ID NO:33), YLQQNWWTL (SEQ ID NO:6), LLVDLLWLL (SEQ ID NO:3), LLLIAIWNL (SEQ ID NO:4), TLLVDLLWL (SEQ ID NO:7), RLGATIWQL (SEQ ID NO:1), SLVIVTTFV (SEQ ID NO:17), LMII-PLINV (SEQ ID NO:20), TLFIGSHVV (SEQ ID NO:24), and VLQWASLAV (SEQ ID NO:27).

3. The isolated peptide of claim 2 wherein the cytotoxic T-cell epitope has an amino acid sequence selected from the group consisting of YLLEMLWRL (SEQ ID NO:1), YLLEILWRL (SEQ ID NO:33), YLQQNWWTL (SEQ ID NO:6), SLVIVTTFV (SEQ ID NO:17), LMIIPLINV (SEQ ID NO:20), TLFIGSHVV (SEQ ID NO:24), and VLQWASLAV (SEQ ID:NO:27).

4. An isolated nucleic acid comprising a nucleotide sequence encoding a peptide consisting of a cytotoxic T-cell epitope having an amino acid sequence selected from the group consisting of YLLEMLWRL (SEQ ID NO:1), YFLEILWGL (SEQ ID NO:32), YLLEILWRL (SEQ ID NO:33), YLQQNWWTL (SEQ ID NO:6), LLLALLFWL (SEQ ID NO:2), LLVDLLWLL (SEQ ID NO:3), LLLIAL-WNL (SEQ ID NO:4), WLLLFLAIL (SEQ ID NO:5), TLLVDLLWL (SEQ ID NO:7), LLWLLLFLA (SEQ ID NO:8), ILLIIALYL (SEQ ID NO:9), VLFIFGCLL (SEQ ID NO:10), RLGATIWQL (SEQ ID NO:11), ILYFIAFAL (SEQ ID NO:15), SLVIVTTFV (SEQ ID NO:17), LMII-PLINV (SEQ ID NO:20), TLFIGSHVV (SEQ ID NO:24), LIPETVPYI (SEQ ID NO:26), VLQWASLAV (SEQ ID NO:27) and QLTPHTKAV (SEQ ID NO:29).

5. The isolated nucleic acid as claimed in claim 4 wherein the epitope has a sequence selected from the group consisting of YLLEMLWRL (SEQ ID NO:1), YLQQNWWTL (SEQ ID NO:6), YFLEILWGL (SEQ ID NO:32), YLLEIWRL (SEQ ID NO:33), SLVIVTTFV (SEQ ID NO:17), LMIIPLINV (SEQ:ID NO:20), TLFIGSHVV (SEQ ID NO:24), and VLQWASLAV (SEQ ID NO:27).

6. The isolated nucleic acid of claim 4 wherein the cytotoxic T-cell epitope has an amino acid sequence selected from the group consisting of YLLEMLWRL (SEQ ID NO:1), YLLEILWRL (SEQ ID NO:33), YLQQNWWTL (SEQ ID NO:6), LLVDLLWLL (SEQ ID NO:3), LLLIALWNL (SEQ ID NO:4), TLLVDLLWL (SEQ ID NO:7), RLGATIWQL (SEQ ID NO. 11), SLVIVTTFV (SEQ ID NO:17), LMIIPLINV (SEQ ID NO:20), TLFIGSHVV (SEQ ID NO:24), and VLQWASLAV (SEQ ID NO:27).

7. The isolated nucleic acid of claim 4 wherein the cytotoxic T-cell epitope has an amino acid sequence selected from the group consisting of YLLEMLWRL (SEQ ID NO:1), YLLEILWRL (SEQ ID NO:33), YLQQNWWTL (SEQ ID NO:6), SLVIVTTFV (SEQ ID NO:17), LMIIPLINV (SEQ ID NO:20), TLFIGSHVV (SEQ ID NO:24), and VLQWASLAV (SEQ ID NO:27).

8. The isolated nucleic acid of claim 6 wherein the cytotoxic T-cell epitope has an amino acid sequence selected from the group consisting of YLLEMLWRL (SEQ ID NO:1), LLVDLLWLL (SEQ ID NO:3), LLLIALWNL (SEQ ID NO:4), YLQQNWWTL (SEQ ID NO:6), TLLVDLLWL (SEQ ID NO:7) and RLGATIWQL (SEQ ID NO:11).

9. A vaccinia virus vector comprising the isolated nucleic acid of claim 8.

10. A vector comprising an isolated nucleic acid as claimed in claim 4.

11. The vector as claimed in claim 10 consisting of a bacterial vector.

12. The vector as claimed in claim 11 wherein the bacterial vector is Salmonella spp.

13. The vector as claimed in claim 10 consisting of a virus vector.

14. The vector as claimed in claim 13 wherein the virus vector is selected from the group consisting of Adenovirus vector, Retrovirus vector, and Vaccinia vector.

15. The vector as claimed in claim 14 wherein the Vaccinia vector is a Modified Vaccinia Ankara.

16. An isolated polypeptide comprising a plurality of isolated Epstein-Barr virus (EBV) CTL epitopes selected from the group consisting of YLLEMLWRL (SEQ ID NO:1), YFLEILWGL (SEQ ID NO:32), YLLEILWRL (SEQ ID NO:33), YLOONWWTL (SEQ ID NO:6). LLLALLFWL (SEQ ID NO:2), LLVDLLWLL (SEQ ID NO:3), LLLIALWNL (SEQ ID NO.4), WLLLFLAIL (SEQ ID NO:5). TLLVDLLWL (SEQ ID NO:7), LLWLLLFLA (SEQ ID NO:8). ILLIIALYL (SEQ ID NO:9). VLFIFGCLL (SEQ ID NO:10). RLGATIWQL (SEQ ID NO:11), ILYFIAFAL (SEQ ID NO:15), SLVIVTTFV (SEQ ID NO:17), LMIIPLINV.(SEQ ID NO:20). TLFIGSHVV (SEQ ID NO:24). LIPETVPYI (SEQ ID NO:26). VLQWASLAV (SEQ ID NO:27) and QLTPHTKAV (SEQ ID NO:29).

17. A method of preparing a composition for use in inducing CTLs in a subject, the method comprising admixing at least one peptide selected from the group consisting of YLLEMLWRL (SEQ ID NO:1), YFLEILWGL (SEQ ID NO:32), YLLEILWRL (SEQ ID NO:33), YLOQNWWTL (SEQ ID NO:6), LLLALLFWL (SEQ ID NO:2), LLVDLLWLL (SEQ ID NO:3), LLLIALWNL (SEQ ID N0:4), WLLLFLAIL (SEQ ID NO:5), TLLVDLLWL (SEQ ID NO;7), LLWLLLFLA (SEQ ID NO:8), ILLIIALYL (SEQ ID NO:9). VLFIFGCLL (SEQ ID NO:10), RLGATIWQL (SEQ ID NO:11), ILYFIAFAL (SEQ ID NO:15). SLVIVTTFV (SEQ ID NO:17). LMIIPLINV (SEQ ID NO:20). TLFIGSHVV (SEQ ID NO:24). LIPETVPYI (SEQ ID NO:26), VLQWASLAV (SEQ ID NO:27) and OLTPHTKAV (SEQ ID NO:29). with a pharmaceutically acceptable carrier, diluent or excipient.

* * * * *

UNITED STATES PATENT AND TRADEMARK OFFICE
CERTIFICATE OF CORRECTION

PATENT NO.    : 6,723,695 B1  
DATED         : April 20, 2004  
INVENTOR(S)   : Scott Renton Burrows, Rajiv Khanna and Martina Alison Sherritt It is certified that error appears in the above-identified patent and that said Letters Patent is hereby corrected as shown below:

Title page,  
Item [75], Inventors, please delete "Bald Hill" and insert -- Queensland -- therefor, please delete "Herston" and insert -- Queensland -- therefor, please delete "Kedron" and insert -- Queensland -- therefor.

Column 40,  
Line 12, please delete "YLOONWWTL" and insert -- YLQQNWWTL -- therefor.  
Line 26, please delete "YLOQNWWTL" and insert -- YLQQNWWTL -- therefor.  
Lines 35-36, please delete "OLTPHTKAV" and insert -- QLTPHTKAV -- therefor.

Signed and Sealed this

Third Day of August, 2004

JON W. DUDAS  
*Acting Director of the United States Patent and Trademark Office*

SEQUENCE LISTING

<160> NUMBER OF SEQ ID NOS: 33

<210> SEQ ID NO 1
<211> LENGTH: 9
<212> TYPE: PRT
<213> ORGANISM: Epstein Barr Virus

<400> SEQUENCE: 1

Tyr Leu Leu Glu Met Leu Trp Arg Leu
 1               5

<210> SEQ ID NO 2
<211> LENGTH: 9
<212> TYPE: PRT
<213> ORGANISM: Epstein Barr Virus

<400> SEQUENCE: 2

Leu Leu Leu Ala Leu Leu Phe Trp Leu
 1               5

<210> SEQ ID NO 3
<211> LENGTH: 9
<212> TYPE: PRT
<213> ORGANISM: Epstein Barr Virus

<400> SEQUENCE: 3

Leu Leu Val Asp Leu Leu Trp Leu Leu
 1               5

<210> SEQ ID NO 4
<211> LENGTH: 9
<212> TYPE: PRT
<213> ORGANISM: Epstein Barr Virus

<400> SEQUENCE: 4

Leu Leu Leu Ile Ala Leu Trp Asn Leu
 1               5

<210> SEQ ID NO 5
<211> LENGTH: 9
<212> TYPE: PRT
<213> ORGANISM: Epstein Barr Virus

<400> SEQUENCE: 5

Trp Leu Leu Leu Phe Leu Ala Ile Leu
 1               5

<210> SEQ ID NO 6
<211> LENGTH: 9
<212> TYPE: PRT
<213> ORGANISM: Epstein Barr Virus

<400> SEQUENCE: 6

Tyr Leu Gln Gln Asn Trp Trp Thr Leu
 1               5

<210> SEQ ID NO 7
<211> LENGTH: 9
<212> TYPE: PRT
<213> ORGANISM: Epstein Barr Virus

<400> SEQUENCE: 7

Thr Leu Leu Val Asp Leu Leu Trp Leu

<210> SEQ ID NO 8
<211> LENGTH: 9
<212> TYPE: PRT
<213> ORGANISM: Epstein Barr Virus

<400> SEQUENCE: 8

Leu Leu Trp Leu Leu Leu Phe Leu Ala
 1               5

<210> SEQ ID NO 9
<211> LENGTH: 9
<212> TYPE: PRT
<213> ORGANISM: Epstein Barr Virus

<400> SEQUENCE: 9

Ile Leu Leu Ile Ile Ala Leu Tyr Leu
 1               5

<210> SEQ ID NO 10
<211> LENGTH: 9
<212> TYPE: PRT
<213> ORGANISM: Epstein Barr Virus

<400> SEQUENCE: 10

Val Leu Phe Ile Phe Gly Cys Leu Leu
 1               5

<210> SEQ ID NO 11
<211> LENGTH: 9
<212> TYPE: PRT
<213> ORGANISM: Epstein Barr Virus

<400> SEQUENCE: 11

Arg Leu Gly Ala Thr Ile Trp Gln Leu
 1               5

<210> SEQ ID NO 12
<211> LENGTH: 9
<212> TYPE: PRT
<213> ORGANISM: Epstein Barr Virus

<400> SEQUENCE: 12

Phe Leu Met Gly Thr Tyr Lys Arg Val
 1               5

<210> SEQ ID NO 13
<211> LENGTH: 9
<212> TYPE: PRT
<213> ORGANISM: Epstein Barr Virus

<400> SEQUENCE: 13

Trp Leu Ala Lys Ser Phe Phe Glu Leu
 1               5

<210> SEQ ID NO 14
<211> LENGTH: 9
<212> TYPE: PRT
<213> ORGANISM: Epstein Barr Virus

<400> SEQUENCE: 14

Gly Leu Tyr Glu Glu Arg Ala His Val
 1               5

<210> SEQ ID NO 15
<211> LENGTH: 9
<212> TYPE: PRT
<213> ORGANISM: Epstein Barr Virus

<400> SEQUENCE: 15

Ile Leu Tyr Phe Ile Ala Phe Ala Leu
 1               5

<210> SEQ ID NO 16
<211> LENGTH: 9
<212> TYPE: PRT
<213> ORGANISM: Epstein Barr Virus

<400> SEQUENCE: 16

Gln Leu Leu Cys Val Phe Cys Leu Val
 1               5

<210> SEQ ID NO 17
<211> LENGTH: 9
<212> TYPE: PRT
<213> ORGANISM: Epstein Barr Virus

<400> SEQUENCE: 17

Ser Leu Val Ile Val Thr Thr Phe Val
 1               5

<210> SEQ ID NO 18
<211> LENGTH: 9
<212> TYPE: PRT
<213> ORGANISM: Epstein Barr Virus

<400> SEQUENCE: 18

Val Leu Ala Ile Ile Leu Tyr Phe Ile
 1               5

<210> SEQ ID NO 19
<211> LENGTH: 9
<212> TYPE: PRT
<213> ORGANISM: Epstein Barr Virus

<400> SEQUENCE: 19

Ile Ile Leu Tyr Phe Ile Ala Phe Ala
 1               5

<210> SEQ ID NO 20
<211> LENGTH: 9
<212> TYPE: PRT
<213> ORGANISM: Epstein Barr Virus

<400> SEQUENCE: 20

Leu Met Ile Ile Pro Leu Ile Asn Val
 1               5

<210> SEQ ID NO 21
<211> LENGTH: 9
<212> TYPE: PRT
<213> ORGANISM: Epstein Barr Virus

<400> SEQUENCE: 21

Met Gln Leu Leu Cys Val Phe Cys Leu
 1               5

<210> SEQ ID NO 22

```
<211> LENGTH: 9
<212> TYPE: PRT
<213> ORGANISM: Epstein Barr Virus

<400> SEQUENCE: 22

Phe Cys Leu Val Leu Leu Trp Glu Val
 1               5

<210> SEQ ID NO 23
<211> LENGTH: 9
<212> TYPE: PRT
<213> ORGANISM: Epstein Barr Virus

<400> SEQUENCE: 23

Tyr Leu Leu Leu Thr Thr Asn Gly Thr
 1               5

<210> SEQ ID NO 24
<211> LENGTH: 9
<212> TYPE: PRT
<213> ORGANISM: Epstein Barr Virus

<400> SEQUENCE: 24

Thr Leu Phe Ile Gly Ser His Val Val
 1               5

<210> SEQ ID NO 25
<211> LENGTH: 9
<212> TYPE: PRT
<213> ORGANISM: Epstein Barr Virus

<400> SEQUENCE: 25

Val Leu Thr Leu Leu Leu Leu Leu Val
 1               5

<210> SEQ ID NO 26
<211> LENGTH: 9
<212> TYPE: PRT
<213> ORGANISM: Epstein Barr Virus

<400> SEQUENCE: 26

Leu Ile Pro Glu Thr Val Pro Tyr Ile
 1               5

<210> SEQ ID NO 27
<211> LENGTH: 9
<212> TYPE: PRT
<213> ORGANISM: Epstein Barr Virus

<400> SEQUENCE: 27

Val Leu Gln Trp Ala Ser Leu Ala Val
 1               5

<210> SEQ ID NO 28
<211> LENGTH: 9
<212> TYPE: PRT
<213> ORGANISM: Epstein Barr Virus

<400> SEQUENCE: 28

Leu Leu Leu Leu Val Met Ala Asp Cys
 1               5

<210> SEQ ID NO 29
<211> LENGTH: 9
<212> TYPE: PRT
```

-continued

```
<213> ORGANISM: Epstein Barr Virus

<400> SEQUENCE: 29

Gln Leu Thr Pro His Thr Lys Ala Val
 1               5

<210> SEQ ID NO 30
<211> LENGTH: 9
<212> TYPE: PRT
<213> ORGANISM: Epstein Barr Virus

<400> SEQUENCE: 30

Met Leu Val Leu Gln Trp Ala Ser Leu
 1               5

<210> SEQ ID NO 31
<211> LENGTH: 9
<212> TYPE: PRT
<213> ORGANISM: Epstein Barr Virus

<400> SEQUENCE: 31

Thr Leu Leu Leu Leu Leu Val Met Ala
 1               5

<210> SEQ ID NO 32
<211> LENGTH: 9
<212> TYPE: PRT
<213> ORGANISM: Epstein Barr Virus

<400> SEQUENCE: 32

Tyr Phe Leu Glu Ile Leu Trp Gly Leu
 1               5

<210> SEQ ID NO 33
<211> LENGTH: 9
<212> TYPE: PRT
<213> ORGANISM: Epstein Barr Virus

<400> SEQUENCE: 33

Tyr Leu Leu Glu Ile Leu Trp Arg Leu
 1               5
```